United States Patent
Sato et al.

(10) Patent No.: US 8,032,320 B2
(45) Date of Patent: Oct. 4, 2011

(54) POSITION DETECTION SYSTEM AND POSITION DETECTION METHOD

(75) Inventors: Ryoji Sato, Hino (JP); Akio Uchiyama, Yokohama (JP); Atsushi Kimura, Akiruno (JP)

(73) Assignee: Olympus Corporation, Tokyo (JP)

( * ) Notice: Subject to any disclaimer, the term of this patent is extended or adjusted under 35 U.S.C. 154(b) by 649 days.

(21) Appl. No.: 12/159,189

(22) PCT Filed: Dec. 25, 2006

(86) PCT No.: PCT/JP2006/325764
§ 371 (c)(1),
(2), (4) Date: Jun. 25, 2008

(87) PCT Pub. No.: WO2007/074767
PCT Pub. Date: Jul. 5, 2007

(65) Prior Publication Data
US 2010/0219825 A1    Sep. 2, 2010

(30) Foreign Application Priority Data

Dec. 28, 2005 (JP) ................................. 2005-377866

(51) Int. Cl.
*G01C 17/38* (2006.01)
(52) U.S. Cl. ........................................................ 702/94
(58) Field of Classification Search .................. 702/94, 702/150–153; 600/109, 421
See application file for complete search history.

(56) References Cited

U.S. PATENT DOCUMENTS 6,847,837 B1 * 1/2005 Melzer et al. ................. 600/421
2003/0229268 A1 * 12/2003 Uchiyama et al. ............ 600/109

FOREIGN PATENT DOCUMENTS

| JP | 2005-40342 | 2/2005 |
| JP | 2006-271520 | 10/2006 |
| WO | WO 2004/014225 A1 | 2/2004 |
| WO | WO 2005/120345 A2 | 12/2005 |

* cited by examiner

*Primary Examiner* — Drew A Dunn
*Assistant Examiner* — Xiuquin Sun
(74) *Attorney, Agent, or Firm* — Scully, Scott, Murphy & Presser, P.C.

(57) ABSTRACT

A position detection system and method in which the accuracy of position measurement of a device is not decreased with changes in the resonant frequency. The system includes a device having a magnetic induction coil; a driving coil generating an alternating magnetic field, applied to the magnetic induction coil, having a position-calculating frequency in the vicinity of a resonant frequency of the magnetic induction coil; a plurality of magnetic sensors that detects an induced magnetic field generated by the magnetic induction coil; a measurement-reference-value calculating section determining a measurement reference value at the position-calculating frequency when only the alternating magnetic field is applied; a position-analyzing section calculating at least one of the position and orientation of the device and the measurement reference value when the alternating magnetic field and the induced magnetic field are applied; and a redetermining section redetermining the position-calculating frequency at a predetermined timing.

12 Claims, 16 Drawing Sheets

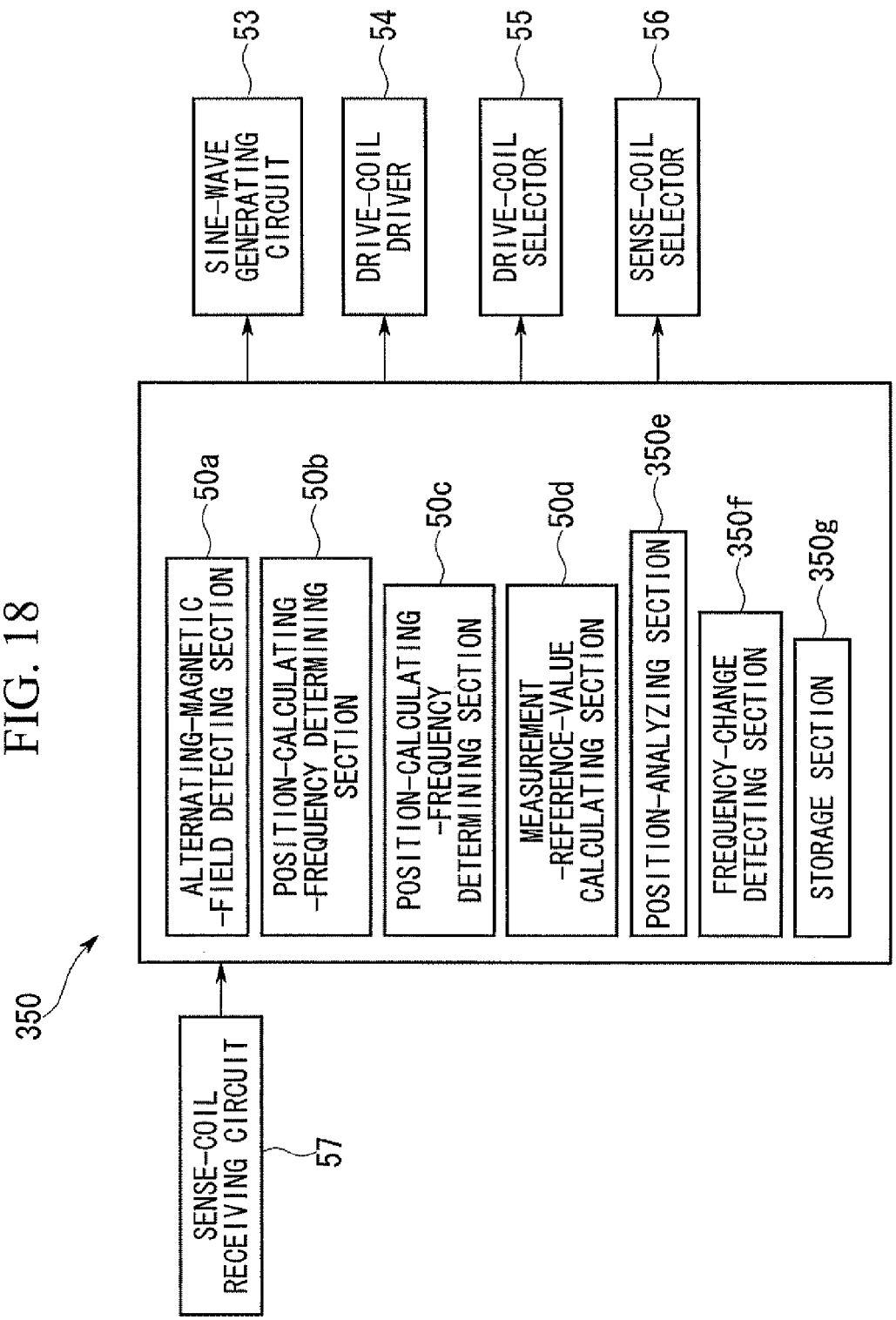

United States Patent US 8,032,320 B2

POSITION DETECTION SYSTEM AND POSITION DETECTION METHOD

TECHNICAL FIELD

The present invention relates to position detection systems and position detection methods for devices having magnetic induction coils, particularly, medical devices for medical use.

BACKGROUND ART

Devices for medical use, or medical devices, include swallowable medical devices (particularly, capsule medical devices) that are swallowed by a subject to enter the subject's body, where they can traverse a passage in the body cavity to capture images of a target site inside the passage in the body cavity. The capsule medical devices described above have a configuration in which an image-acquisition device that can be used for the above medical treatment, for example, a charge-coupled device (CCD), which can acquire images, is provided for performing image acquisition at the target site inside the passage in the body cavity.

However, the above-described capsule medical device has to be guided through the passage in the body cavity in order to reach a target site. To guide the capsule medical device, it is necessary to detect its position in the passage in the body cavity.

Therefore, some techniques have been proposed for detecting the position of, for example, a capsule medical device guided to a site where its position cannot be visually checked (such as a body cavity). (For example, see Patent Document 1.)

Patent Document 1:
PCT International Publication No. WO 2004/014225 Pamphlet

DISCLOSURE OF INVENTION

Patent Document 1 above discloses a position detection technique for a capsule medical device, using a capsule medical device provided with a magnetic-field generating circuit including an LC resonant circuit connected to an AC power supply and a detection device that is disposed outside the capsule medical device and that detects a magnetic field generated by the magnetic-field generating circuit.

According to this technique, the magnetic-field generating circuit generates an externally directed magnetic field on the basis of the AC electric power supplied from the AC power supply. The detection device can then detect the position of the capsule medical device by detecting the magnetic field.

According to the above-described technique for position detection, however, the magnetic-field generating circuit including the LC resonant circuit connected to the AC power supply is disposed inside the capsule medical device. This makes it difficult to reduce the size of the capsule medical device. There is therefore a problem in that the above technique is not suitable for a capsule medical device that is small enough to be easily swallowed by the subject.

If the size of the capsule medical device is reduced, the size of the AC power supply is reduced accordingly, thus limiting the electric power that can be supplied to the magnetic-field generating circuit. Consequently, the intensity of the magnetic field generated by the magnetic-field generating circuit is reduced, and position detection of the capsule medical device becomes difficult. There is therefore a problem in that the above technique is not suitable for capsule medical devices. In addition, the life of the AC power supply is shortened, and the life of the capsule medical device is shorted accordingly. There is therefore a problem in that the above technique is not suitable for capsule medical devices.

Also known is a position detection technique for a capsule medical device, using a capsule medical device incorporating an LC resonant circuit composed only of a magnetic induction coil and a capacitor, drive coils that are disposed outside the subject's body and that cause the magnetic induction coil to generate an induced electromotive force, and a plurality of externally disposed magnetic sensors that detects the induced magnetic field.

According to this technique, first, the magnetic induction coil in the LC resonant circuit produces an induced magnetic field by the induced electromotive force induced by the drive coils. The magnetic sensors then detect the induced magnetic field, so that the position of the capsule medical device can be detected. In other words, according to this technique, since the position of the capsule medical device can be detected without installing an AC power supply inside the capsule medical device, the size of the capsule medical device can be easily reduced, position detection becomes easy, and the life of the device can be increased.

During the detection of the capsule medical device, the drive coils generate an alternating magnetic field, acting upon the LC resonant circuit, that has two different frequencies slightly higher and lower than the resonant frequency of the LC resonant circuit.

According to the above-described position detection technique, however, since the magnetic sensors simultaneously detect the driving magnetic field generated by the drive coils and the induced magnetic field generated by the magnetic induction coil, it is difficult to detect the position of the capsule medical device because the induced magnetic field is buried in the driving magnetic field.

It is known that the induced magnetic field can be calculated by measuring only the driving magnetic field of the drive coils in advance (calibration measurement), with the magnetic induction coil disposed outside the detection range, and then subtracting the measured driving magnetic field from the simultaneously detected driving magnetic field and induced magnetic field in order to remove only the driving magnetic field from the simultaneously detected driving magnetic field and induced magnetic field.

The frequency of the driving magnetic field under the calibration measurement must be the same as the frequency of the driving magnetic field used for the position detection of the capsule medical device.

The above-described method, however, has a problem in that the calibration measurement must always be performed on the driving magnetic field used before the position detection of the capsule medical device, thus making the position detection inefficient.

The resonant frequency of the LC resonant circuit is determined by the characteristics of the magnetic induction coil and the capacitor included in the LC resonant circuit. The characteristics of the magnetic induction coil and the capacitor change with, for example, the temperatures of the magnetic induction coil and the capacitor. Accordingly, the resonant frequency of the LC resonant circuit may change with the environment (such as temperature) surrounding the capsule medical device.

Hence, position detection of the capsule medical device will be performed with a driving magnetic field of a different frequency from the resonant frequency of the LC resonant circuit if the environment surrounding the capsule medical device when the resonant frequency of the LC resonant circuit is determined differs from the environment surrounding the capsule medical device when the capsule medical device is introduced into the subject's body.

This decreases the intensity of the magnetic field generated by the magnetic induction coil in response to the driving magnetic field, thus causing the problem of decreased measurement accuracy of the position of the capsule medical device.

One solution to the above problem is a technique of adjusting the resonant frequency of the LC resonant circuit by providing the LC resonant circuit with a capacitor whose capacitance can be adjusted (variable capacitor) or a coil whose frequency characteristics can be adjusted (coil whose core position can be adjusted).

Such devices as variable capacitors and coils, however, have adjustment mechanisms that make it difficult to reduce the size of the capsule medical device. There is therefore a problem in that the above technique is not suitable for capsule medical devices.

To adjust such variable devices, the power supply in the capsule must be used, and its capacity must be increased accordingly. This makes it difficult to reduce the size of the capsule medical device. There is therefore a problem in that the above technique is not suitable for capsule medical devices.

If the capacity of the power supply is not increased, the operating time of the capsule is decreased. There is therefore a problem in that the above technique is not suitable for capsule medical devices.

An object of the present invention, which has been made to solve the problems described above, is to provide a position detection system and a position detection method in which the accuracy of position measurement of a device is not decreased after a change in the resonant frequency of a magnetic induction coil.

To achieve the above-described object, the present invention provides the following solutions.

According to a first aspect of the present invention, there is provided a position detection system including a device having a magnetic induction coil; a driving coil that generates an alternating magnetic field, to be applied to the magnetic induction coil, having a position-calculating frequency in the vicinity of a resonant frequency of the magnetic induction coil; a plurality of magnetic sensors that detects an induced magnetic field generated by the magnetic induction coil when the alternating magnetic field is applied thereto; a measurement-reference-value calculating section that determines a measurement reference value at the position-calculating frequency, based on an output of the magnetic sensors at the position-calculating frequency when only the alternating magnetic field is applied thereto; a position-analyzing section that calculates at least one of the position and orientation of the device, based on a component at the position-calculating frequency of a difference measurement value that is a difference between an output of the magnetic sensors when the alternating magnetic field and the induced magnetic field are applied thereto and the measurement reference value; and a redetermining section that redetermines the position-calculating frequency at a predetermined timing.

To calculate at least one of the position and orientation of the device in the first aspect of the present invention, first, the measurement-reference-value calculating section determines the measurement reference value based on the position-calculating frequency when only the alternating magnetic field is applied to the magnetic sensors. The position-analyzing section then calculates at least one of the position and orientation of the device based on the component at the position-calculating frequency of the difference measurement value, which is the difference between the output of the magnetic sensors when the alternating magnetic field and the induced magnetic field are applied thereto, and the measurement reference value.

The redetermining section is provided to redetermine the position-calculating frequency at a predetermined timing. Hence, even if frequency characteristics related to the magnetic induction coil (one of the frequency characteristics is the resonant frequency) are changed with, for example, changes in temperature or environment, the position or orientation of the device can be detected with the position-calculating frequency based on the changed frequency characteristics. This allows the use of the optimum position-calculating frequency at any time, thus avoiding a decrease in the measurement accuracy of the position and so on of the device.

In the first aspect of the present invention, the redetermining section preferably redetermines the position-calculating frequency at predetermined time intervals.

By doing so, because the redetermining section redetermines the position-calculating frequency at predetermined time intervals, even if the frequency characteristics related to the magnetic induction coil are changed with, for example, changes in temperature or environment, the position or orientation of the device can be detected with the optimum position-calculating frequency based on the changed frequency characteristics.

The timing of redetermination of the optimum position-calculating frequency is based on predetermined time intervals. This method can simplify the system configuration in comparison with, for example, the method of redetermination based on changes in the frequency characteristics related to the magnetic induction coil.

In a preferred configuration of the first aspect of the present invention, the position detection system further includes a frequency-change detecting section that detects a change in frequency characteristics related to the magnetic induction coil from magnetic-field information obtained by the plurality of magnetic sensors, and the redetermining section redetermines the position-calculating frequency based on the change in the frequency characteristics.

By doing so, because the position detection system includes the frequency-change detecting section that detects a change in the frequency characteristics related to the magnetic induction coil and the redetermining section redetermines the position-calculating frequency based on the detected change in the frequency characteristics, even if the frequency characteristics related to the magnetic induction coil are changed with, for example, changes in temperature or environment, the position or orientation of the device can be detected with the optimum position-calculating frequency based on the changed frequency characteristics.

The timing of redetermination of the position-calculating frequency is based on changes in the frequency characteristics. This method allows detection of the position or orientation of the device with the optimum position-calculating frequency even if the frequency characteristics related to the magnetic induction coil are suddenly changed, in comparison with, for example, the method of redetermination based on predetermined time intervals.

In the above configuration, preferably, the frequency-change detecting section detects the change in the frequency characteristics based on the magnetic-field information, and the magnetic-field information is obtained by sweeping over a predetermined frequency range including the position-calculating frequency.

By doing so, the frequency-change detecting section can detect a change in the frequency characteristics related to the magnetic induction coil because it detects the change in the frequency characteristics based on the magnetic-field information obtained by sweeping over the predetermined frequency range including the position-calculating frequency.

Even if the frequency characteristics related to the magnetic induction coil are changed, the frequency-change detecting section can detect the changed frequency characteristics because the frequency-change detecting section performs the sweeping over the predetermined frequency range, which includes the frequency of the changed frequency characteristics.

In the above configuration, preferably, the position-calculating frequency includes two different frequencies in the vicinity of the resonant frequency, and the frequency-change detecting section calculates the ratio of the difference measurement values at the two different frequencies and detects the change in the frequency characteristics based on the calculated ratio of the difference measurement values.

By doing so, the frequency-change detecting section can detect a change in the frequency characteristics related to the magnetic induction coil because it detects the change in the frequency characteristics based on the ratio of the difference measurement values at the two different frequencies.

The frequency-change detecting section can detect a change in the frequency characteristics because the difference-measurement-value ratio before the frequency characteristics are changed differs from that after the frequency characteristics are changed. Specifically, the difference-measurement-value ratio is the ratio of the difference measurement values at the two different frequencies in the vicinity of the resonant frequency. As the frequency characteristics are changed, the difference measurement values at the two different frequencies are changed, and the difference-measurement-value ratio is changed accordingly. The frequency-change detecting section can detect the change in the frequency characteristics by detecting the change in the difference-measurement-value ratio.

In the above configuration, preferably, the position-calculating frequency includes two different frequencies in the vicinity of the resonant frequency, the frequency-change detecting section calculates the ratio of the difference measurement values at the two different frequencies and detects the change in the frequency characteristics based on the calculated ratio of the difference measurement values, and the position detection system further includes an arithmetic section that calculates the resonant frequency based on the difference measurement values at the two different frequencies.

By doing so, because the arithmetic section is provided, it can determine, for example, a changed resonant frequency of the magnetic induction coil based on the difference measurement values at the two different frequencies. This allows determination of position-calculating frequencies that are two different frequencies in the vicinity of the changed resonant frequency.

The difference measurement values at the two frequencies are changed with a change in the resonant frequency. In addition, since the two frequencies are different frequencies, the rate of change with the change in the resonant frequency differs between the difference measurement values at the two frequencies. The arithmetic section can therefore determine the changed resonant frequency based on the changes in the difference measurement values at the two frequencies by calculation.

In the above configuration, preferably, the position detection system further includes a storage section that stores the resonant frequency, and the frequency-change detecting section detects the change in the frequency characteristics based on the difference measurement value calculated at the resonant frequency retrieved from the storage section.

By doing so, because the storage section is provided, the frequency-change detecting section can detect a change in the frequency characteristics related to the magnetic induction coil based on the difference measurement value at the resonant frequency retrieved from the storage section.

If, for example, the resonant frequency of the magnetic induction coil is equal to the resonant frequency stored in the storage section, the difference measurement value calculated at the resonant frequency is zero. If the resonant frequency of the magnetic induction coil is changed and therefore no longer agrees with the resonant frequency stored in the storage section, the difference measurement value calculated at the resonant frequency stored in the storage section is a value other than zero.

Thus, the frequency-change detecting section can detect a change in the frequency characteristics related to the magnetic induction coil based on the difference measurement value calculated at the resonant frequency stored in the storage section.

The difference measurement value calculated at the stored resonant frequency is zero if the frequency is equal to the resonant frequency of the magnetic induction coil and is a value other than zero in other cases. This method can determine whether or not the resonant frequency stored in the storage section is equal to the resonant frequency of the magnetic induction coil more accurately than, for example, the method using a difference-measurement-value ratio of two different frequencies in the vicinity of the resonant frequency. This contributes to increased responsiveness to changes in the resonant frequency of the magnetic induction coil.

In the above configuration, preferably, the position detection system further includes a storage section that stores the resonant frequency, the frequency-change detecting section detects the change in the frequency characteristics based on the difference measurement value calculated at the resonant frequency retrieved from the storage section, the position detection system further includes an arithmetic section that calculates the resonant frequency to be stored in the storage section, and the arithmetic section calculates the resonant frequency based on the difference measurement value at the resonant frequency retrieved from the storage section and the difference measurement values at a plurality of the position-calculating frequencies.

By doing so, the arithmetic section can calculate a changed resonant frequency of the magnetic induction coil because the arithmetic section calculates the resonant frequency based on the difference measurement value at the resonant frequency retrieved from the storage section and the difference measurement values at the plurality of position-calculating frequencies. As a result, the redetermining section can redetermine the position-calculating frequency based on the redetermined resonant frequency.

The arithmetic section calculates a changed resonant frequency using the difference measurement values at the plurality of position-calculating frequencies in addition to the difference measurement value at the resonant frequency retrieved from the storage section. This method allows more accurate calculation of the changed resonant frequency than, for example, the method of calculating a changed resonant frequency using only the difference measurement value at the resonant frequency retrieved from the storage section.

In the above configuration, preferably, the position detection system further includes a storage section that stores the resonant frequency, the frequency-change detecting section detects the change in the frequency characteristics based on the difference measurement value calculated at the resonant frequency retrieved from the storage section, the position detection system further includes an arithmetic section that calculates the resonant frequency to be stored in the storage section, the arithmetic section calculates the resonant frequency based on the difference measurement value at the resonant frequency retrieved from the storage section and the difference measurement values at a plurality of the position-calculating frequencies, and the arithmetic section calculates the resonant frequency based on the difference measurement value at the resonant frequency stored in the storage section and, of the difference measurement values at the plurality of position-calculating frequencies, a difference measurement value having a different sign from the difference measurement value at the stored resonant frequency.

By doing so, because the arithmetic section calculates the resonant frequency of the magnetic induction coil based on the difference measurement value at the resonant frequency stored in the storage section and, of the difference measurement values at the position-calculating frequencies, a difference measurement value having a different sign from the difference measurement value at the stored resonant frequency, even if the resonant frequency of the magnetic induction coil is significantly changed, the arithmetic section can accurately redetermine the changed resonant frequency. As a result, the position-calculating-frequency determining section can redetermine the position-calculating frequencies based on the redetermined resonant frequency.

On a graph illustrating the frequency characteristics related to the magnetic induction coil, a line segment can be formed between the difference measurement value at the stored resonant frequency and, of the difference measurement values at the position-calculating frequencies, the difference measurement value having a different sign from the difference measurement value at the stored resonant frequency. If the resonant frequency of the magnetic induction coil is significantly changed, the line segment approximates to a curve representing the frequency characteristics in the vicinity of the resonant frequency of the magnetic induction coil. With the line segment, therefore, the arithmetic section can more accurately redetermine the resonant frequency of the magnetic induction coil after a significant change in the resonant frequency.

In the first aspect of the present invention, preferably, the position-analyzing section calculates a first magnetic-field strength of the alternating magnetic field from the magnetic induction coil based on the output of the magnetic sensors and the measurement reference value and also calculates the positional relationship between the device and the driving coil, and the frequency-change detecting section detects the change in the frequency characteristics based on a difference between the first magnetic-field strength and a second magnetic-field strength, determined from the positional relationship between the device and the driving coil, of the alternating magnetic field from the magnetic induction coil.

By doing so, the position-analyzing section calculates the first magnetic-field strength when calculating the position of the magnetic induction coil. The frequency-change detecting section then calculates the second magnetic-field strength from the relationship between the calculated position and orientation of the magnetic induction coil and the position and orientation of the drive coil. If the frequency characteristics of the magnetic induction coil are changed, the first and second magnetic-field strengths have different values. The frequency-change detecting section can then detect the change in the frequency characteristics of the magnetic induction coil by comparing the first and second magnetic-field strengths.

Of the strengths of the magnetic field generated by the magnetic induction coil, the first magnetic-field strength is a magnetic-field strength carrying information about the actual positional relationship between the drive coil and the magnetic induction coil. The second magnetic-field strength is a magnetic-field strength calculated from the positional relationship between the position of the drive coil and the calculated position of the magnetic induction coil and the value of the resonant frequency.

In the first aspect of the present invention, the device is preferably a capsule medical device.

By doing so, because the device is a capsule medical device, the device can be introduced into a subject's body to perform medical treatment, such as observation or administration, inside the body cavity of the subject.

According to a second aspect of the present invention, there is provided a position detection method for detecting at least one of the position and orientation of a device having a magnetic induction coil based on an induced magnetic field generated by the magnetic induction coil when an alternating magnetic field having a position-calculating frequency is applied thereto. This method includes the steps of calculating at least one of the position and orientation of the device based on the induced magnetic field; detecting a change in the resonant frequency of the magnetic induction coil; redetermining the position-calculating frequency from the change in the resonant frequency; and applying an alternating magnetic field having the redetermined position-calculating frequency to the magnetic induction coil to generate an induced magnetic field.

According to the second aspect of the present invention, the detection accuracy of the position or orientation of the device can be maintained at a high level because the above method includes the steps of detecting a change in the resonant frequency of the magnetic induction coil; redetermining the position-calculating frequency from the change in the resonant frequency; and applying an alternating magnetic field having the redetermined position-calculating frequency to the magnetic induction coil to generate an induced magnetic field.

That is, even if the resonant frequency of the magnetic induction coil is changed with, for example, changes in temperature or environment, the change can be detected because the above method includes the step of detecting a change in the resonant frequency of the magnetic induction coil. The optimum position-calculating frequency based on the changed frequency characteristics can be used at any time because the above method includes the step of redetermining the position-calculating frequency from the change in the resonant frequency. The position or orientation of the device can be detected with the optimum position-calculating frequency because the above method includes the step of applying an alternating magnetic field having the redetermined position-calculating frequency to the magnetic induction coil to generate an induced magnetic field.

According to the position detection method of the present invention, even if the resonant frequency of the magnetic induction coil is changed with, for example, changes in temperature or environment, the position or orientation of the device can be detected at any time with the optimum position-calculating frequency based on the changed frequency characteristics. As a result, the detection accuracy of the position or orientation of the device can be maintained at a high level.

In the second aspect of the present invention, the step of calculating at least one of the position and orientation of the device based on the induced magnetic field preferably includes the steps of determining as a measurement reference value a magnetic-field strength detected at the position-calculating frequency when only the alternating magnetic field acts; and calculating at least one of the position and orientation of the device based on a difference between a magnetic-field strength of a combined magnetic field of the alternating magnetic field and the induced magnetic field and the measurement reference value.

By doing so, at least one of the position and orientation of the device can be accurately calculated because the step of calculating at least one of the position and orientation of the device based on the induced magnetic field includes the steps of determining as the measurement reference value the magnetic-field strength detected at the position-calculating frequency when only the alternating magnetic field acts; and calculating at least one of the position and orientation of the device based on the difference between the magnetic-field strength of the combined magnetic field of the alternating magnetic field and the induced magnetic field and the measurement reference value.

The magnetic-field strength of the induced magnetic field alone can be determined by subtracting the measurement reference value from the magnetic-field strength of the combined magnetic field. Based on the magnetic-field strength of the induced magnetic field alone, therefore, at least one of the position and orientation of the device can be accurately calculated.

According to the present invention, the redetermining section is provided to redetermine the position-calculating frequency at a predetermined timing. Hence, even if the frequency characteristics related to the magnetic induction coil are changed with, for example, changes in temperature or environment, the position or orientation of the device can be detected with the position-calculating frequency based on the changed frequency characteristics. This allows the use of the optimum position-calculating frequency at any time, thus providing the advantage of avoiding a decrease in the measurement accuracy of the position and so on of the device.

BRIEF DESCRIPTION OF DRAWINGS

FIG. 18 is a block diagram illustrating the internal structure of a position detection device shown in FIG. 17.

Figure 1:
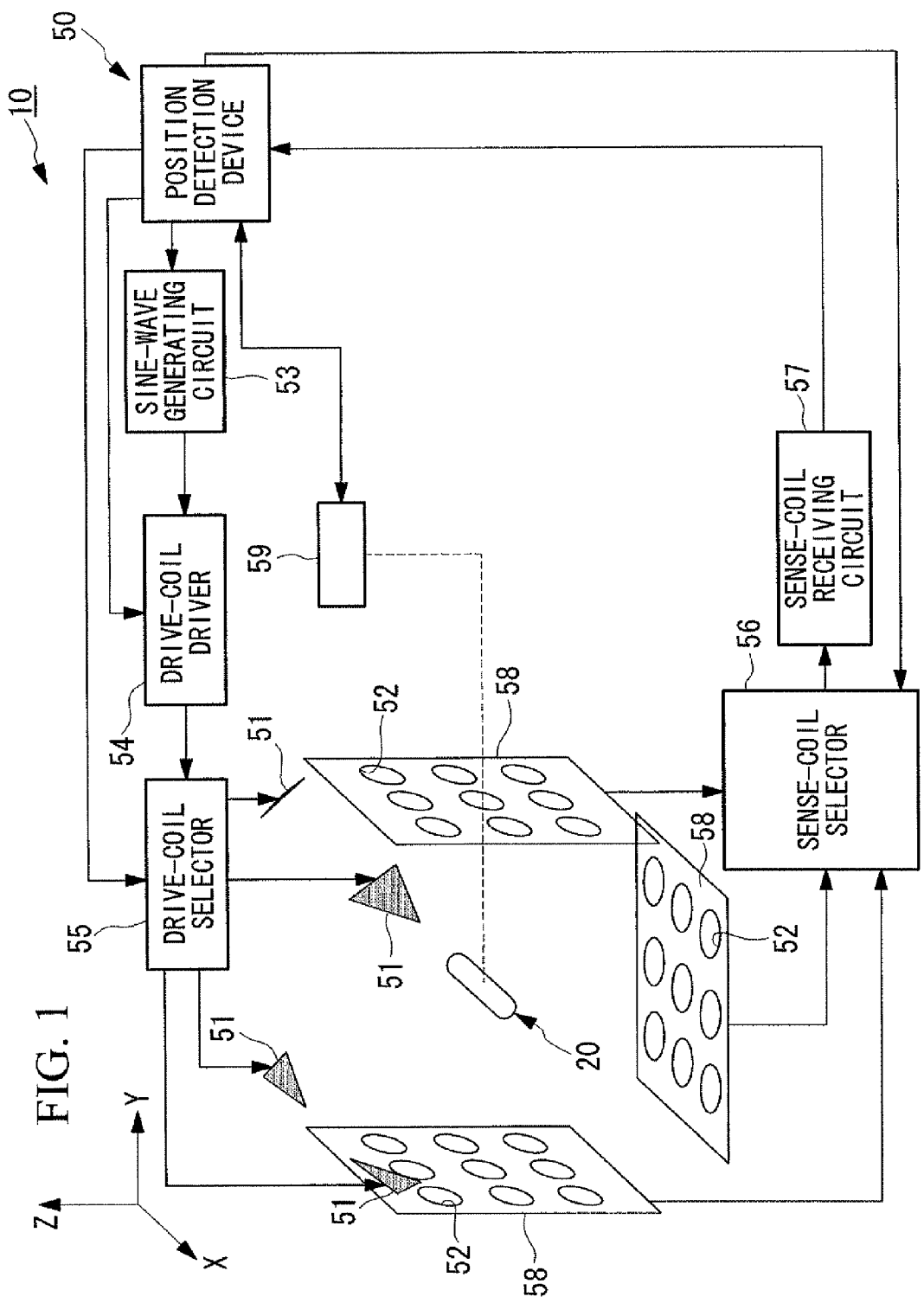
FIG. 1 is a schematic view illustrating the overall structure of a position detection system according to a first embodiment of the present invention.

EXPLANATION OF REFERENCE SIGNS 10, 110, 210, and 310: position detection system
20: capsule endoscope (device or capsule medical device)
42: magnetic induction coil
50, 150, 250, and 350: position detection device (position-analyzing section)
50b: position-calculating-frequency determining section
50d: measurement-reference-value calculating section
50e and 350e: position-analyzing section
51: drive coil (driving coil)
52: sense coil (magnetic sensor)
150f, 250f, and 350f: frequency-change detecting section
250g and 350g: storage section
150h and 250h: arithmetic section
$f_H$ and $f_L$: position-calculating frequency
$f_C$: resonant frequency

BEST MODE FOR CARRYING OUT THE INVENTION

First Embodiment

A position detection system according to a first embodiment of the present invention will be described below with reference to FIGS. 1 to 10.

Figure 2:
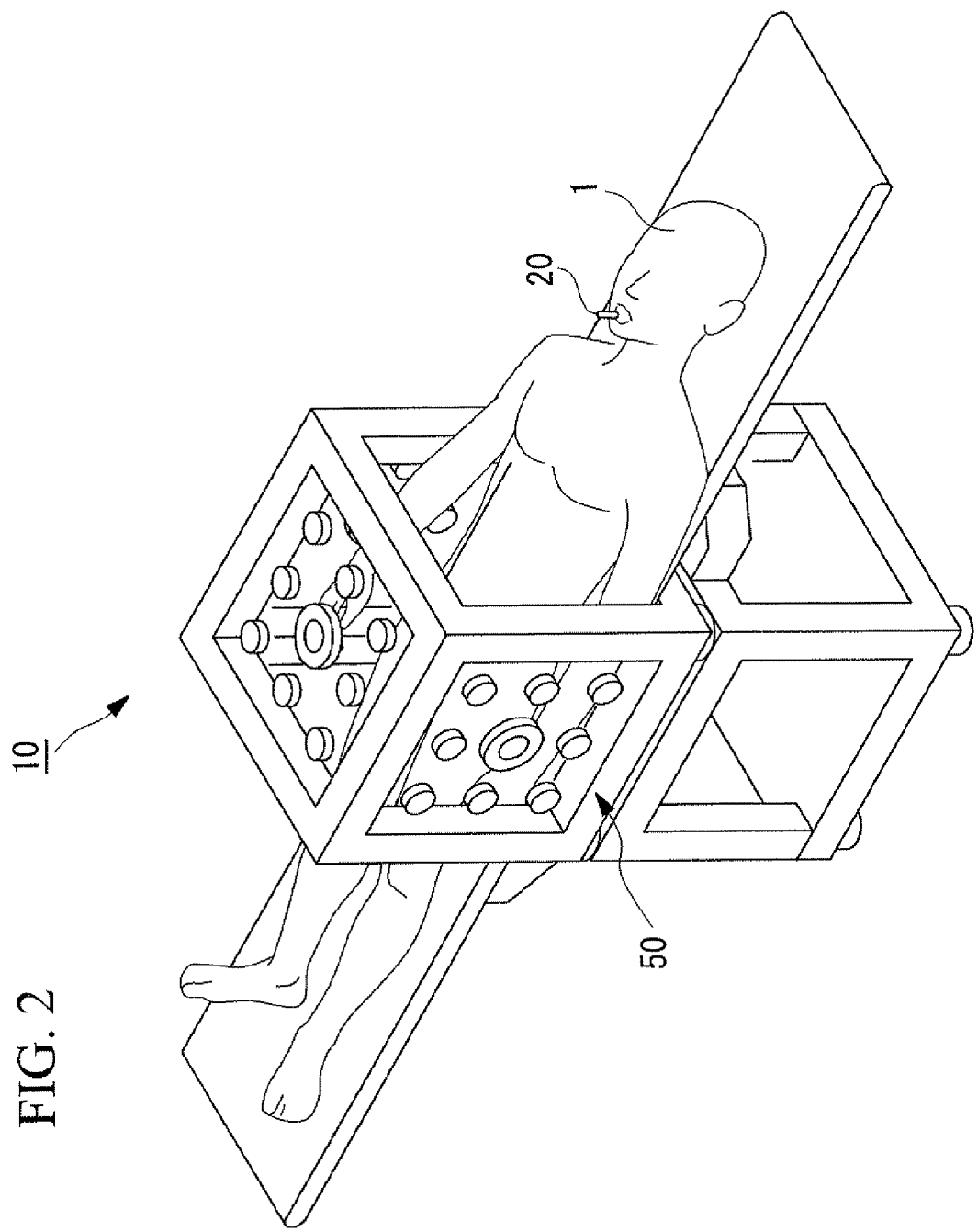
FIG. 2 is a perspective view illustrating the exterior of the position detection system shown in FIG. 1.

FIG. 1 is a schematic view illustrating the overall structure of the position detection system according to this embodiment. FIG. 2 is a perspective view illustrating the exterior of the position detection system shown in FIG. 1.

As shown in FIGS. 1 and 2, a position detection system 10 mainly includes a capsule endoscope (device or capsule medical device) 20, which is a capsule medical device that is introduced into a body cavity of a subject 1 per oral or per anus to optically image an internal surface of a passage in the body cavity and to wirelessly transmit image signals, and a position detection device (position-analyzing section) 50 that detects the position of the capsule endoscope 20.

The capsule medical device is not limited to the above-described capsule endoscope; instead, it may be a capsule medical device that administers a drug at a predetermined site in the body cavity or that obtains a sample, such as body fluid, or biological information.

As shown in FIG. 1, the position detection device 50 is electrically connected to, for example, drive coils (driving coils) 51 that cause a magnetic induction coil, described below, in the capsule endoscope 20 to generate an induced magnetic field and sense coils (magnetic sensors) 52 that detect the induced magnetic field generated by the magnetic induction coil. The position detection device 50 calculates the position of the capsule endoscope 20 on the basis of the induced magnetic field detected by the sense coils 52 and controls an alternating magnetic field formed by the drive coils 51.

Figure 3:
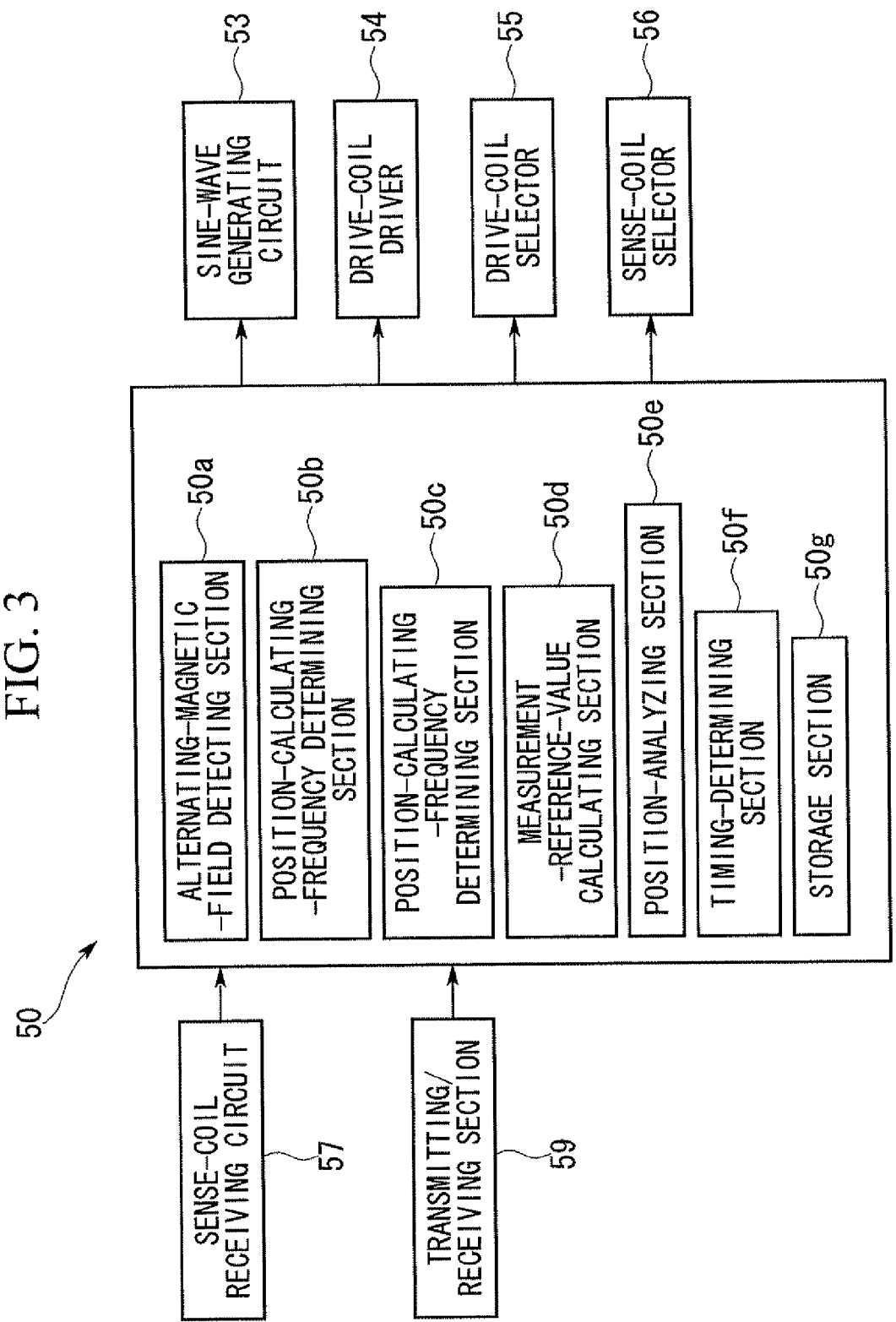
FIG. 3 is a block diagram illustrating the internal structure of a position detection device shown in FIG. 1.

FIG. 3 is a block diagram illustrating the internal structure of the position detection device shown in FIG. 1.

In FIG. 3, the position detection device 50 includes an alternating-magnetic-field detecting section 50a, a position-calculating-frequency determining section (redetermining section) 50b, a reference-value-calculating-frequency determining section 50c, a measurement-reference-value calculating section 50d, a position-analyzing section 50e, a timing-determining section 50f, and a storage section 50g.

The alternating-magnetic-field detecting section 50a detects an amplitude value of an alternating magnetic field from an AC voltage (magnetic-field information) output from the sense coils 52.

The position-calculating-frequency determining section 50b determines and redetermines position-calculating frequencies $f_H$ and $f_L$ used for calculating the position and so on of the capsule endoscope 20.

The reference-value-calculating-frequency determining section 50c determines a reference-value-calculating frequency f1 used for calculating measurement reference values.

The measurement-reference-value calculating section 50d calculates the measurement reference values from the outputs of the sense coils 52 at the position-calculating frequencies $f_H$ and $f_L$ and the reference-value-calculating frequency f1.

The position-analyzing section 50e calculates the position and so on of the capsule endoscope 20.

The timing-determining section 50f informs the position-calculating-frequency determining section 50b about a timing at which the frequency of a resonant frequency $f_C$ is redetermined.

The storage section 50g stores, for example, the reference values calculated by the measurement-reference-value calculating section 50d.

Between the position detection device 50 and the drive coils 51, as shown in FIG. 1, there are provided a sine-wave generating circuit 53 that generates an AC current, a drive-coil driver 54 that amplifies the AC current, and a drive-coil selector 55 that supplies the AC current to the drive coils 51.

The sine-wave generating circuit 53 generates an AC current based on the output of the position detection device 50. The drive-coil driver 54 amplifies the AC current input from the sine-wave generating circuit 53 based on the output of the position detection device 50. The drive-coil selector 55 supplies the AC current to a drive coil 51 selected on the basis of the output of the position detection device 50.

Between the sense coils 52 and the position detection device 50, there are provided a sense-coil selector 56 and a sense-coil receiving circuit 57.

The sense-coil selector 56 selects an AC current, containing information about, for example, the position of the capsule endoscope 20, output from a particular sense coil 52 of the plurality of sense coils 52 on the basis of the output of the position detection device 50. The sense-coil receiving circuit 57 extracts an amplitude value of AC voltage from the AC current that has passed through the sense-coil selector 56 and outputs the amplitude value to the position detection device 50.

The position detection device 50 is provided with a transmitting/receiving section 59 that transmits and receives, for example, image signals or resonant frequency values to and from the capsule endoscope 20.

Figure 4:
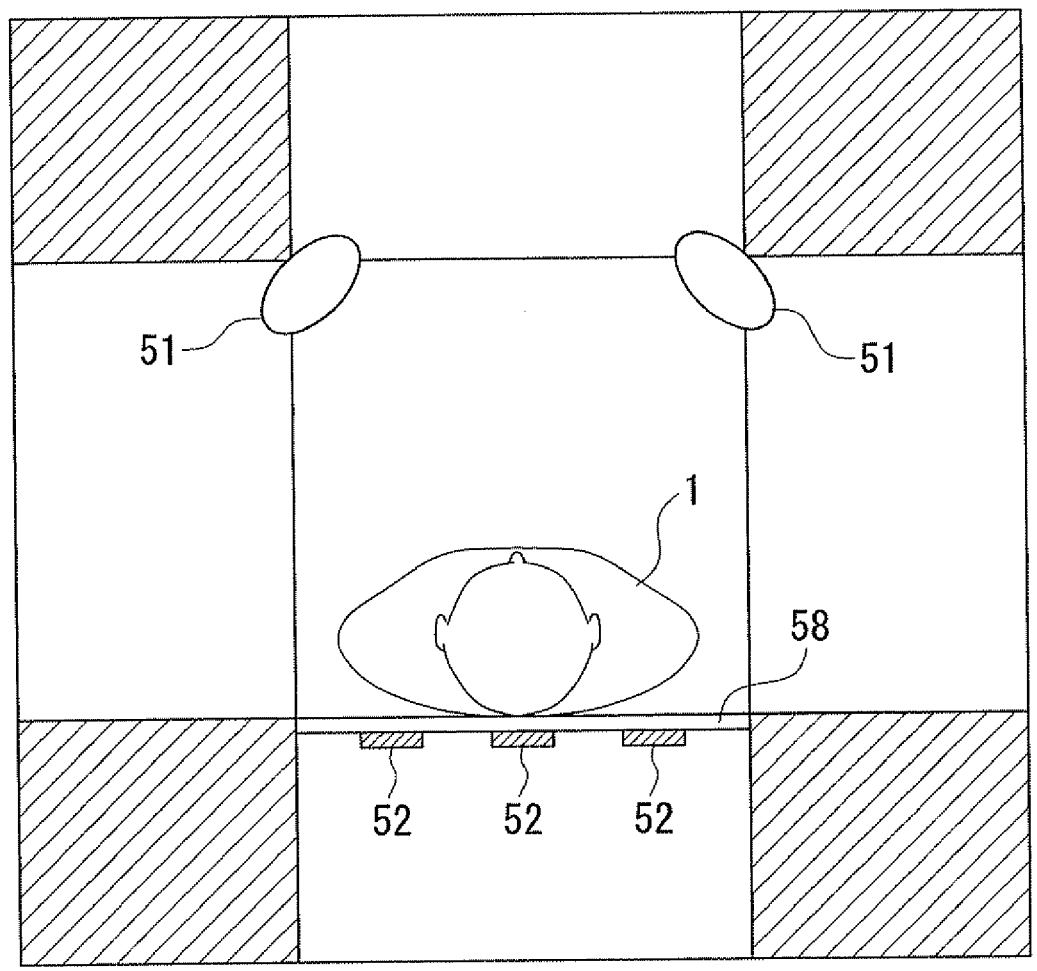
FIG. 4 is a schematic view illustrating a cross-section of a capsule endoscope system shown in FIG. 1.

FIG. 4 is a schematic view illustrating a cross-section of the capsule endoscope system shown in FIG. 1.

As shown in FIGS. 1 and 4, the drive coils 51 are obliquely disposed at the four corners at the top (the positive-direction side of the Z-axis) of a substantially rectangular operating space where the subject 1 lies. The drive coils 51 are formed as substantially triangular coils. By disposing the drive coils 51 at the top in this way, it is possible to prevent interference between the drive coils 51 and the subject 1.

The drive coils 51 may be substantially triangular coils, as mentioned above, or it is possible to use coils of various shapes, such as circular coils.

The sense coils 52 are formed as air-core coils and are supported by three planar coil-supporting parts 58 that are disposed at a position opposite the drive coils 51 and at opposing positions in the Y-axis direction on either side of the operating space of the capsule endoscope 20. Each coil-supporting part 58 has nine sense coils 52 arranged in a matrix, and thus the position detection device 50 has a total of 27 sense coils 52.

Figure 5:
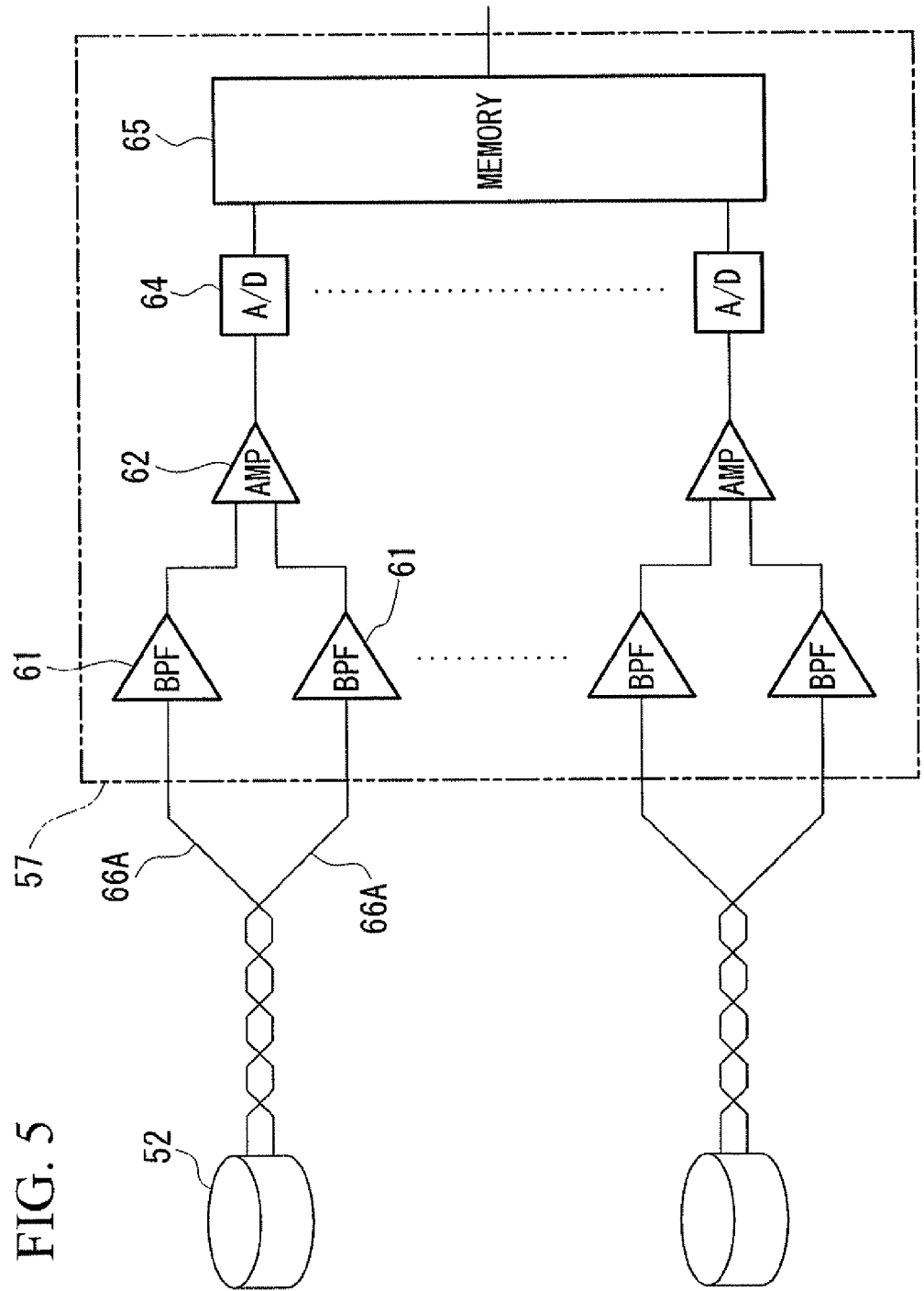
FIG. 5 is a schematic view illustrating the circuit configuration of a sense-coil receiving circuit shown in FIG. 1.

FIG. 5 is a schematic view illustrating the circuit configuration of the sense-coil receiving circuit 57 shown in FIG. 1.

As shown in FIG. 5, the sense-coil receiving circuit 57 includes band-pass filters (BPF) 61 that remove high-frequency components and low-frequency components from the AC voltage, amplifiers (AMP) 62 that amplify the AC voltage, A/D converters 64 that convert the AC voltage to a digital signal, and a memory 65 for temporarily storing a digitized amplitude value.

The band-pass filters (BPF) 61 remove high-frequency components and low-frequency components from the input AC voltage carrying the information about the position of the capsule endoscope 20. The amplifiers (AMP) 62 amplify the AC voltage from which the high-frequency components and low-frequency components have been removed.

The band-pass filters 61 are provided for pairs of wires 66A extending from the sense coils 52, and the AC voltage output from the band-pass filters 61 is input to one of the amplifiers 62. The memory 65 temporarily stores the amplitude value obtained by the nine sense coils 52 and outputs the stored amplitude value to the position detection device 50.

The waveform of the AC voltage detected is shifted in phase with respect to the waveform applied to the drive coil 51 depending on the presence or absence and position of a magnetic induction coil 42, described below, in the capsule endoscope 20. This phase shift may be detected with, for example, a lock-in amplifier.

Figure 6:
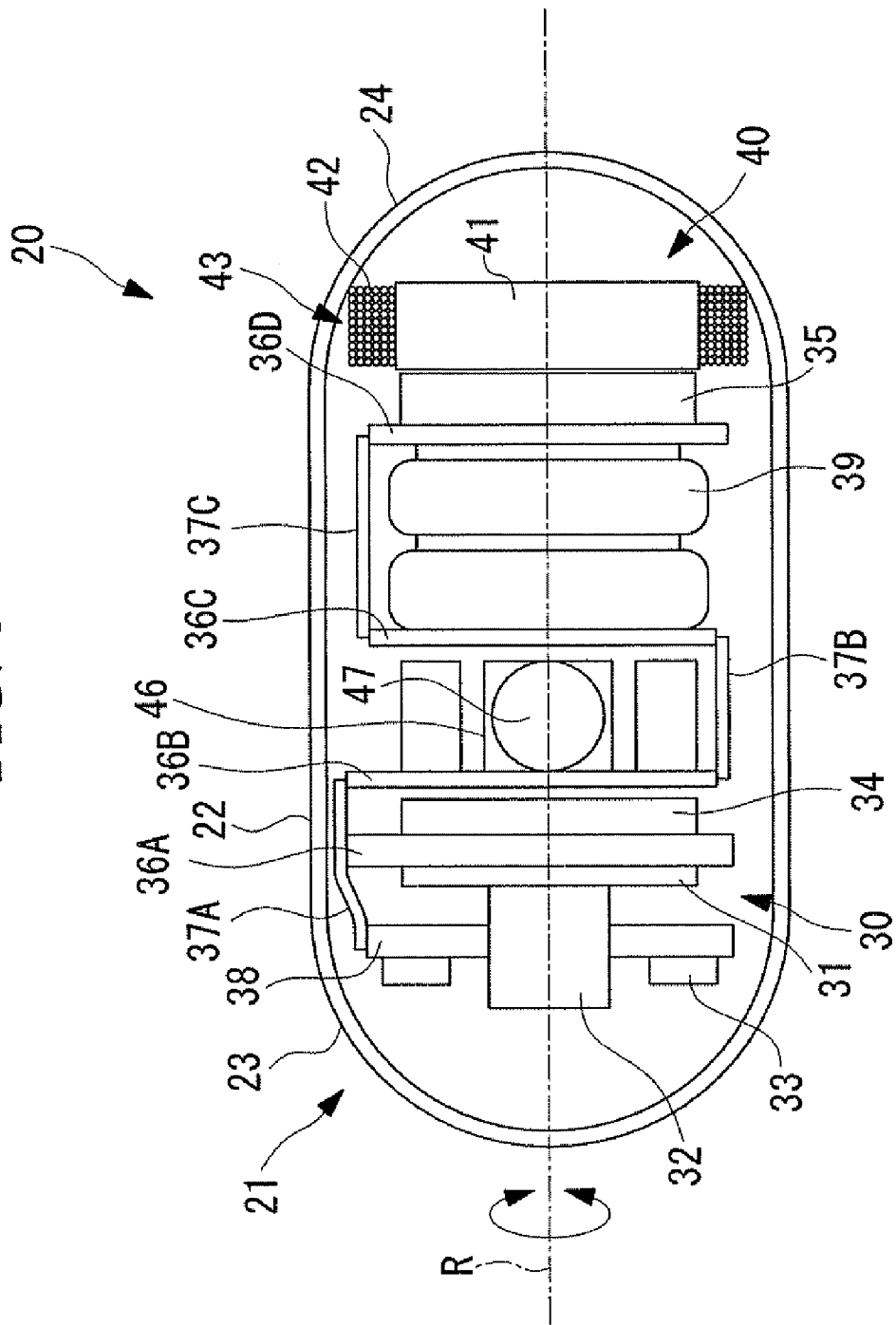
FIG. 6 is a schematic view illustrating the structure of a capsule endoscope shown in FIG. 1.

FIG. 6 is a schematic view illustrating the structure of the capsule endoscope 20 shown in FIG. 1.

As shown in FIG. 6, the capsule endoscope 20 mainly includes an outer casing 21 that accommodates various devices in the interior thereof, an image-acquisition section 30 that images an internal surface of a passage in the body cavity of the subject, a battery 39 for driving the image-acquisition section 30, and an induced-magnetic-field generating section 40 that is caused to generate an induced magnetic field by the drive coils 51 described above.

The outer casing 21 is constituted of an infrared-transmitting cylindrical capsule main body (hereinafter simply referred to as a main body) 22 whose central axis coincides with a rotation axis R of the capsule endoscope 20, a transparent hemispherical front-end portion 23 that covers the front end of the main body 22, and a hemispherical rear-end portion 24 that covers the rear end of the main body, thus forming a sealed capsule container with a watertight construction.

The image-acquisition section 30 mainly includes a board 36A positioned substantially orthogonal to the rotation axis R, an image sensor 31 disposed on a surface of the board 36A on the front-end portion 23 side, a lens group 32 that forms an image of the internal surface of the passage inside the body cavity of the subject on the image sensor 31, a light-emitting diode (LED) 33 that illuminates the internal surface of the passage inside the body cavity, a signal-processing section 34 disposed on a surface of the board 36A on the rear-end portion 24 side, and a wireless element 35 that transmits image signals to an image display device 80.

The signal-processing section 34 is electrically connected to the battery 39 via the board 36A, boards 36B, 36C, and 36D, and flexible boards 37A, 37B, and 37C, is electrically connected to the image sensor 31 via the board 36A, and is electrically connected to the LED 33 via the board 36A, the flexible board 37A, and a support member 38. The signal-processing section 34 compresses and temporarily stores image signals acquired by the image sensor 31 and transmits the compressed image signals from the wireless element 35 to the transmitting/receiving section 59, and also controls the on/off state of the image sensor 31 and the LED 33 based on signals from switch sections 46 to be described later.

In addition, the signal-processing section 34 stores the frequency of the resonant frequency $f_C$ of an LC resonant circuit 43 (magnetic induction coil 42) 43 in the induced-magnetic-field generating section 40. The frequency of the resonant frequency $f_C$ is stored before using the capsule endoscope 20. For example, the frequency of the resonant frequency $f_C$ can be stored during the production of the capsule endoscope 20 or at the same time as inspection prior to shipment.

The image sensor 31 converts an image formed through the front-end portion 23 and the lens group 32 to electrical signals (image signals) and outputs the signals to the signal-processing section 34. The image sensor 31 used may be, for example, a complementary metal-oxide-semiconductor (CMOS) sensor or a CCD sensor.

The plurality of LEDs 33 are disposed on the support member 38, which is positioned closer to the front-end portion 23 than the board 36A, and are arranged at predetermined intervals about the rotation axis R in the circumferential direction.

The switch sections 46 are disposed on the board 36B on the rear-end portion 24 side of the signal-processing section 34. The battery 39 is interposed between the boards 36C and 36D on the rear-end portion 24 side of the switch sections 46. The wireless element 35 is disposed on the board 36D on the rear-end portion 24 side of the battery 39.

The wireless element 35 transmits the image signals compressed by the signal-processing section 34 to the transmitting/receiving section 59 and also transmits the frequency of the resonant frequency $f_C$ of the LC resonant circuit 43, which is stored in the signal-processing section 34 in advance, to the transmitting/receiving section 59.

The switch sections 46 have infrared sensors 47, are electrically connected to the signal-processing section 34 via the boards 36A and 36B and the flexible board 37A, and are electrically connected to the battery 39 via the boards 36B, 36C, and 36D and the flexible boards 37B and 37C.

The plurality of switch sections 46 are arranged at regular intervals about the rotation axis R in the circumferential direction, and the infrared sensors 47 are disposed so as to face the outside in the radial direction. In this embodiment, an example is described in which four switch sections 46 are disposed, but the number of switch sections 46 is not limited to four; any number of switch sections 46 may be provided.

The induced-magnetic-field generating section 40 is disposed on the rear-end portion 24 side of the wireless element 35. The induced-magnetic-field generating section 40 includes a core member 41 made of ferrite formed in the shape of a cylinder whose central axis substantially coincides with the rotation axis R; the magnetic induction coil 42, which is disposed around the outer circumferential part of the core member 41; and a capacitor (not shown) that is electrically connected to the magnetic induction coil 42. The magnetic induction coil 42 and the capacitor form the LC resonance circuit 43.

In addition to ferrite, a material such as iron, permalloy, or nickel may be used for the core member 41.

Next, the operation of the position detection system 10 having the above-described configuration will be described.

First, the operation of the position detection system 10 will be outlined.

As shown in FIG. 2, the capsule endoscope 20 is inserted per oral or anus into the body cavity of the subject 1 lying down inside the position detection device 50. The position of the inserted capsule endoscope 20 is detected by the position detection device 50. The capsule endoscope 20 acquires an image of the internal surface of the passage in the body cavity in the vicinity of an affected area and transmits image-acquisition data about the internal surface of the passage inside the body cavity and image-acquisition data about the vicinity of the affected area to an image display device (not shown).

Next, the operation of the position detection device 50, which is a feature of this embodiment, will be described.

The position detection device 50, as shown in FIG. 1, reads the frequency of the resonant frequency $f_C$ of the LC resonant circuit 43 stored in advance in the signal-processing section 34 of the capsule endoscope 20. Specifically, the position detection device 50 obtains the frequency of the resonant frequency $f_C$ stored in advance in the signal-processing section 34 (see FIG. 6) via the transmitting/receiving section 59 and the wireless element 35.

After obtaining the frequency of the resonant frequency $f_C$, the position detection device 50 outputs signals to the sine-wave generating circuit 53. The sine-wave generating circuit 53 then generates an AC current based on the frequency of the obtained resonant frequency $f_C$ and outputs the generated AC current to the drive-coil driver 54.

The drive-coil driver 54 amplifies the AC current based on an instruction from the position detection device 50 and outputs it to the drive-coil selector 55. The drive-coil selector 55 supplies the amplified AC current to the drive coil 51 selected by the position detection device 50. The AC current supplied to the drive coil 51 produces an alternating magnetic field in the operating space of the capsule endoscope 20.

The alternating magnetic field produces an induced electromotive force that causes an induced current to flow through the magnetic induction coil 42 of the capsule endoscope 20 in the alternating magnetic field. As the induced current flows through the magnetic induction coil 42, it produces an induced magnetic field.

The magnetic induction coil 42 forms the LC resonance circuit 43 together with the capacitor. Hence, if the cycle of the alternating magnetic field matches the resonant frequency of the LC resonance circuit 43, the induced current flowing through the LC resonance circuit 43 (magnetic induction coil 42) is increased, and the induced magnetic field that is formed is intensified accordingly. Furthermore, since the core member 41, formed of dielectric ferrite, is disposed in the center of the magnetic induction coil 42, the induced magnetic field can be easily concentrated at the core member 41, and the induced magnetic field formed is further intensified. The dielectric ferrite may be replaced with a magnetic material such as iron, nickel, or cobalt, and alloys thereof and ferrite, for example, may also be used.

The induced magnetic field produces an induced electromotive force in the sense coils 52, so that an AC voltage (magnetic information) containing information about, for example, the position of the capsule endoscope 20 is generated in the sense coils 52. This AC voltage is input to the sense-coil receiving circuit 57 via the sense-coil selector 56 and is converted to digital signals.

As shown in FIG. 5, the band-pass filters 61 remove high-frequency components and low-frequency components from the AC voltage input to the sense-coil receiving circuit 57 before the AC voltage is amplified by the amplifiers 62. The AC voltage from which the unwanted components have been removed is converted to digital signals by the A/D converter 64 and is stored in the memory 65.

The memory 65 stores, for example, amplitude values corresponding to one cycle in which a sine-wave signal generated by the sine-wave generating circuit 53 is swept near the resonance frequency of the LC resonance circuit 43 and simultaneously outputs one cycle of amplitude values to the position detection device 50.

Figure 7:
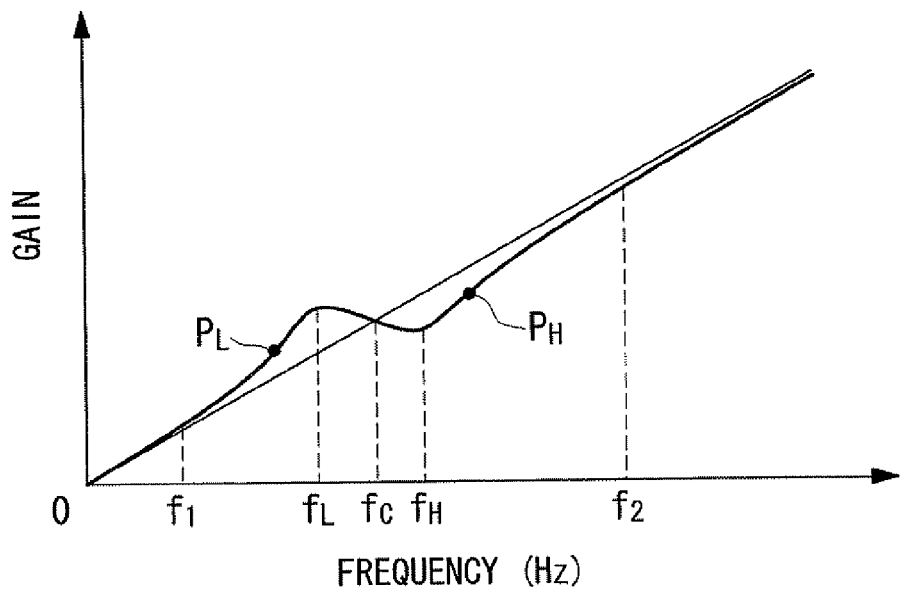
FIG. 7 is a graph illustrating the frequency characteristics of an AC voltage output from sense coils shown in FIG. 1.

FIG. 7 is a graph illustrating the frequency characteristics of the AC voltage output from the sense coils 52 shown in FIG. 1.

The AC voltage input to the position detection device 50, as shown in FIG. 3, is input to the alternating-magnetic-field detecting section 50a. The alternating-magnetic-field detecting section 50a detects the amplitude values of the alternating magnetic field by Fourier transformation. The detected amplitude values of the alternating magnetic field are input to the position-calculating-frequency determining section 50b.

As shown in FIG. 7, the position-calculating-frequency determining section 50b detects the frequencies corresponding to the maximum and minimum values of the AC voltage in a region around the frequency of the resonant frequency $f_C$. The frequencies corresponding to the maximum and minimum values are defined as the position-calculating frequencies $f_H$ and $f_L$, respectively. The frequency of the position-calculating frequency $f_H$ is a frequency higher than the frequency of the resonant frequency $f_C$, whereas the frequency of the position-calculating frequency $f_L$ is a frequency lower than the frequency of the resonant frequency $f_C$.

The reference-value-calculating-frequency determining section 50c defines the frequency of the reference-value calculating frequency f1. The frequency of the reference-value calculating frequency f1 is a frequency that is lower than an inflection point PL on the low-frequency side of the resonant frequency $f_C$ on the frequency-characteristics curve of the AC voltage and that is higher than the frequency of the commercial power supply (60 Hz or 50 Hz). The frequency-characteristics curve of the AC voltage refers to a frequency-characteristics curve, obtained by the position-analyzing section 50e to be described later, of the AC voltage resulting from the induced magnetic field.

Figure 8:
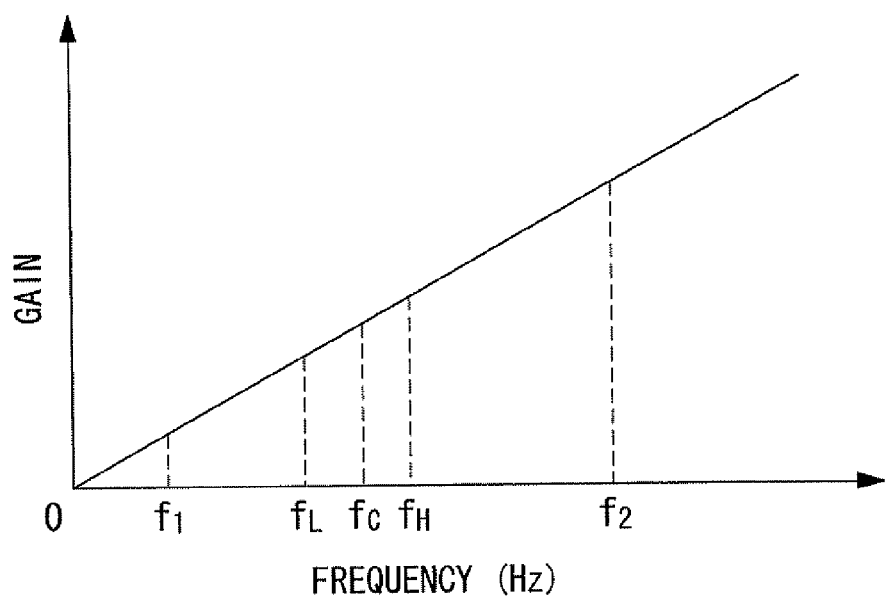
FIG. 8 is a graph illustrating the AC-voltage frequency characteristics of the sense coils shown in FIG. 1 when only an alternating magnetic field acts upon the sense coils.

FIG. 8 is a graph illustrating the AC-voltage frequency characteristics of the sense coils 52 shown in FIG. 1 when only the alternating magnetic field acts upon the sense coils 52.

The measurement-reference-value calculating section 50d calculates measurement reference values from the values of the AC voltage output from the sense coils 52 at the frequencies of the position-calculating frequencies $f_H$ and $f_L$ the frequency of the reference-value calculating frequency f1. Specifically, the values of the AC voltage output from the sense coils 52 at the frequencies of the position-calculating frequencies $f_H$ and $f_L$ are determined, and the average value thereof is determined. Then, a point defined by the intermediate value $((f_H+f_L)/2)$ of the frequencies of the position-calculating frequencies $f_H$ and $f_L$ and the above average value is determined, and a point defined by the reference-value calculating frequency f1 and the corresponding value of the AC voltage is determined. Based on these two points, the measurement reference values are determined. The measurement reference values thus calculated are stored in the storage section 50g.

The measurement reference values can be determined by an approximation method based on the least-squares method. The measurement reference values thus determined can be represented as a graph showing predetermined frequency characteristics, as shown in FIG. 8. The measurement reference values can be assumed as the values of the AC voltage output from the sense coils 52 due to the alternating magnetic field produced by the drive coils 51.

The measurement reference values may be approximate values based on two points, as described above, or may be approximate values based on more than two measurement points.

Figure 9:
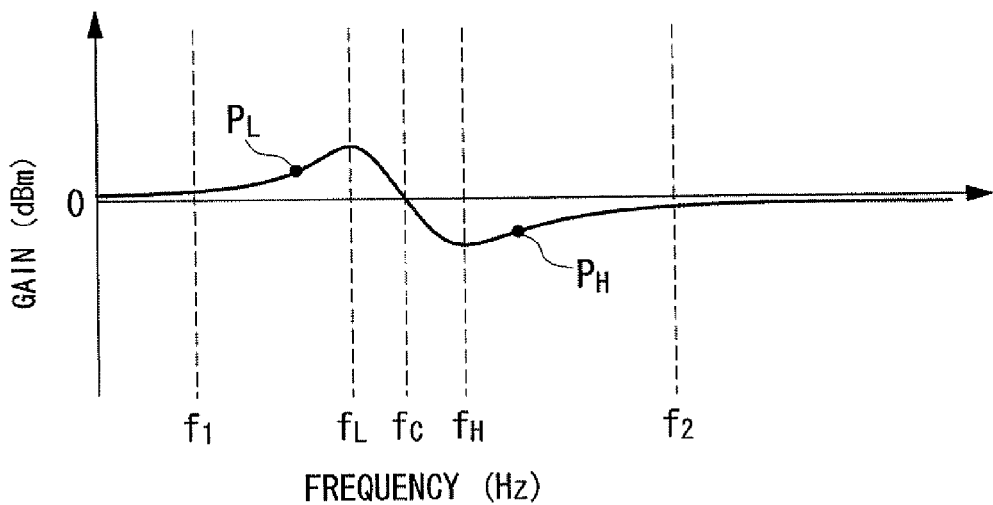
FIG. 9 is a graph illustrating the AC-voltage frequency characteristics of the sense coils shown in FIG. 1 when only an induced magnetic field acts upon the sense coils.

FIG. 9 is a graph illustrating the AC-voltage frequency characteristics of the sense coils 52 shown in FIG. 1 when only the induced magnetic field acts upon the sense coils 52.

First, the position-analyzing section 50e retrieves the measurement reference values stored in the storage section 50g. The position-analyzing section 50e then performs a calculation by subtracting the measurement reference values from the frequency-characteristics curve of the AC voltage output from the sense coils 52, thus obtaining the frequency-characteristics curve of the AC voltage due to the induced magnetic field shown in FIG. 9.

Based on the obtained frequency-characteristics curve, the position-analyzing section 50e calculates the differences in AC voltage at the frequencies of the position-calculating frequencies $f_H$ and $f_L$ for each sense coil 52 to determine difference measurement values. The difference measurement values refer to the amplitude of the frequency-characteristics curve when only the induced magnetic field acts upon the sense coils 52; the position-analyzing section 50e determines this amplitude.

After the amplitude values are obtained for each sense coil 52, the position-analyzing section 50e calculates the position and so on of the capsule endoscope 20 on the basis of these amplitude values.

The remeasurement of the resonant frequency of the LC resonant circuit 43, which is a feature of this embodiment, will now be described with reference to FIG. 10.

Figure 10:
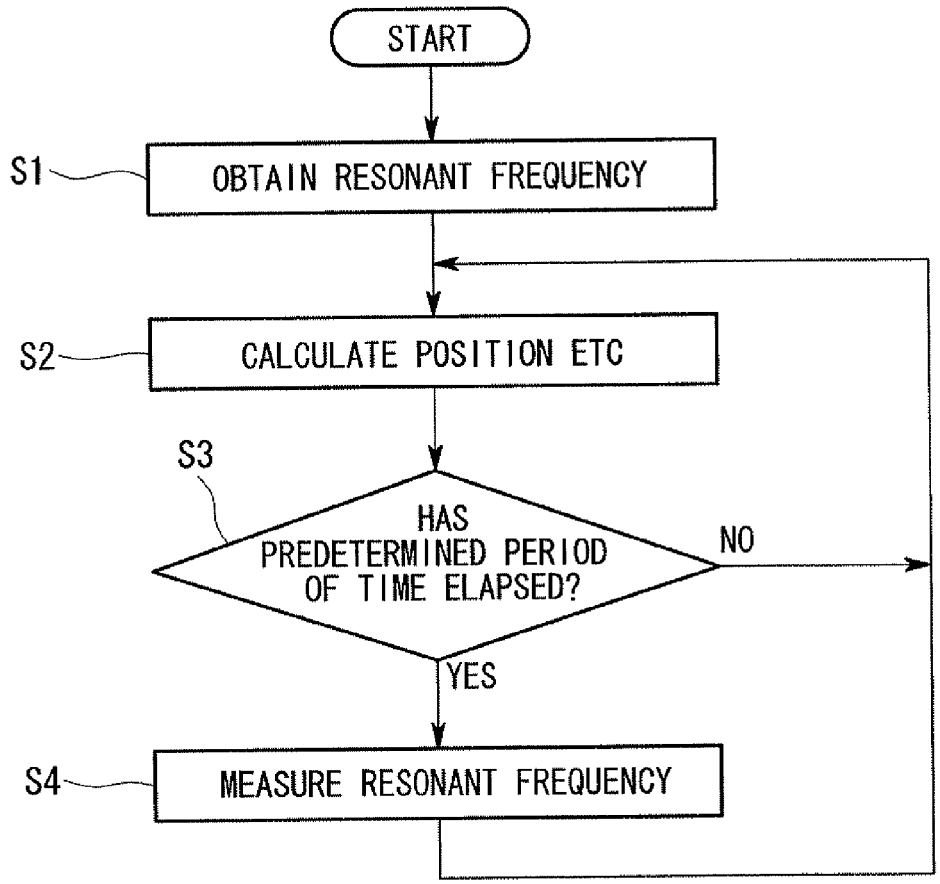
FIG. 10 is a flowchart illustrating the timing of remeasurement of resonant frequency.

FIG. 10 is a flowchart illustrating the timing of remeasurement of the resonant frequency.

In FIG. 10, the position detection device 50 starts the position measurement of the capsule endoscope 20 by obtaining the frequency of the resonant frequency $f_C$ stored in advance in the signal-processing section 34 (see FIG. 6) via the transmitting/receiving section 59 and the wireless element 35 (Step S1).

The position detection device 50 then calculates the position and so on of the capsule endoscope 20, as described above, based on the frequency of the obtained resonant frequency $f_C$ (Step S2).

At the same time, the timing-determining section 50f of the position detection device 50 starts counting time to determine whether or not a predetermined period of time has elapsed (Step S3).

If the timing-determining section 50f determines that the predetermined period of time has elapsed, it outputs a signal to the position-calculating-frequency determining section 50b. In response to the signal input from the timing-determining section 50f, the position-calculating-frequency determining section 50b redetermines the frequencies of new position-calculating frequencies $f_H$ and $f_L$ in a region around the frequency of the resonant frequency $f_C$ (Step S4).

After the frequencies of the new position-calculating frequencies $f_H$ and $f_L$ are redetermined, the position detection device 50 calculates the position and so on of the capsule endoscope 20 based on the frequencies of the new position-calculating frequencies $f_H$ and $f_L$ (Step S2).

Subsequently, the above control is repeated until the detection of the position and so on of the capsule endoscope 20 is terminated.

The above predetermined period of time is the period of time required for the frequency of the resonant frequency $f_C$ of the LC resonant circuit 43 to change to such an extent that it affects the detection accuracy of the position and so on of the capsule endoscope 20. Examples of factors that can change the frequency of the resonant frequency $f_C$ include a change in the temperature of the LC resonant circuit 43 itself.

Next, the redetermination of the frequencies of the new position-calculating frequencies $f_H$ and $f_L$, by the position-calculating-frequency determining section 50b will be described.

When the signal output from the timing-determining section 50f is input to the position-calculating-frequency determining section 50b, the position detection device 50 starts obtaining the frequency of a new resonant frequency $f_C$ based on the output of the position-calculating-frequency determining section 50b.

The position detection device 50, as shown in FIG. 1, causes the drive coils 51 to generate an alternating magnetic field in the operating space of the capsule endoscope 20. The position detection device 50 then controls the sine-wave generating circuit 53 to change (sweep) the frequency of the alternating magnetic field within a predetermined frequency range.

The frequency change is not particularly limited; it may be changed from low to high frequencies or from high to low frequencies. The range over which the frequency is changed may be, for example, several kHz to 100 kHz, although the frequency range is not particularly limited; it may be higher or lower than the above range.

The position detection device 50 calculates the frequency of the new resonant frequency $f_C$ based on amplitude values of the alternating magnetic field obtained by sweeping the frequency of the alternating magnetic field. The amplitude values of the alternating magnetic field are input to the position detection device 50 after the sense-coil receiving circuit 57 processes the output of the sense coils 52.

After the frequency of the new resonant frequency $f_C$ is calculated, the position-calculating-frequency determining section 50b redetermines the frequencies of the new position-calculating frequencies $f_H$ and $f_L$ (see FIG. 3).

The above configuration includes the position-calculating-frequency determining section 50b to redetermine the position-calculating frequencies $f_H$ and $f_L$. Hence, even if the frequency characteristics (related to the magnetic induction coil 42) of the LC resonant circuit 43 are changed with, for example, changes in temperature or environment, the position or orientation of the capsule endoscope 20 can be detected with the position-calculating frequencies $f_H$ and $f_L$ based on the changed frequency characteristics. This allows the use of the optimum position-calculating frequencies $f_H$ and $f_L$ at any time, thus avoiding a decrease in the measurement accuracy of the position and so on of the capsule endoscope 20.

To calculate at least one of the position and orientation of the capsule endoscope 20, first, the measurement-reference-value calculating section 50d determines the measurement reference values based on the position-calculating frequencies $f_H$ and $f_L$ when only the alternating magnetic field acts upon the magnetic sensors 52. The position-analyzing section 50e then calculates at least one of the position and orientation of the capsule endoscope 20 based on the difference between the output of the magnetic sensors 52 when the alternating magnetic field and the induced magnetic field act upon the magnetic sensors 52 and the measurement reference values.

The position-calculating-frequency determining section 50b redetermines the position-calculating frequencies $f_H$ and $f_L$ at predetermined time intervals in response to instructions from the timing-determining section 50f. Hence, even if the frequency characteristics of the LC resonant circuit 43 are changed with, for example, changes in temperature or environment, the position or orientation of the capsule endoscope 20 can be detected with the optimum position-calculating frequencies $f_H$ and $f_L$ based on the changed frequency characteristics.

The timing of redetermination of the optimum position-calculating frequencies $f_H$ and $f_L$, is based on predetermined time intervals. This method can simplify the configuration of the position detection system 10 in comparison with, for example, the method of redetermination based on changes in the frequency characteristics of the LC resonant circuit 43.

Figure 11:
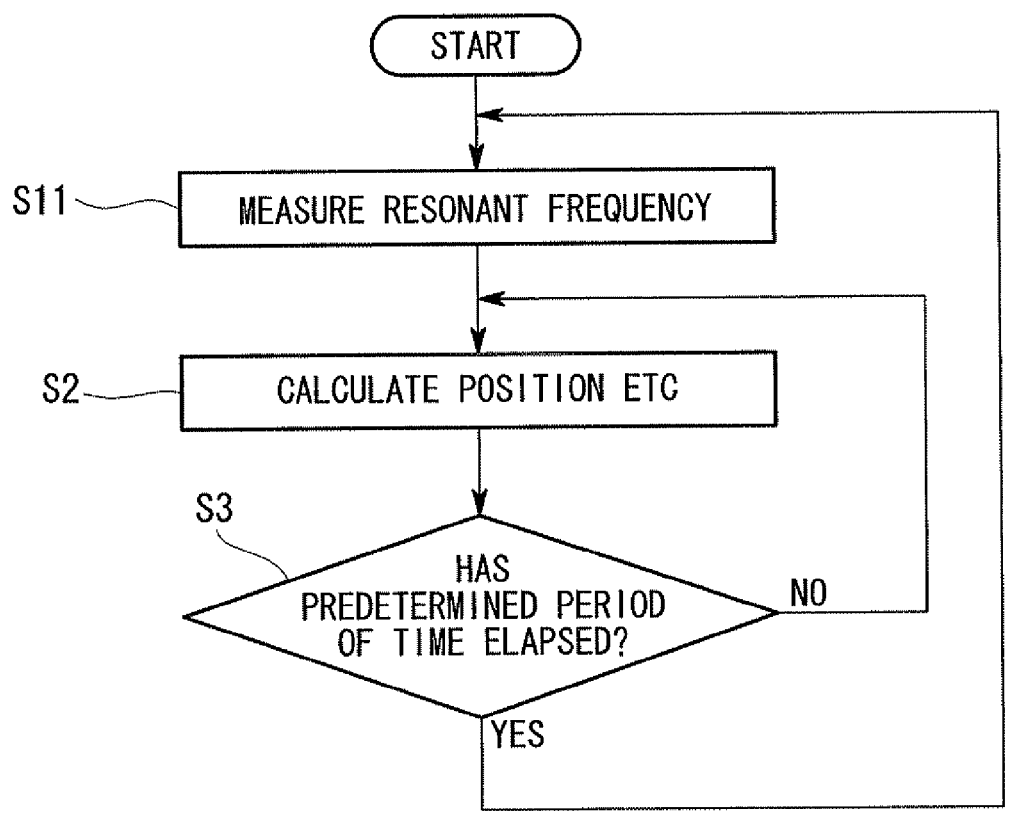
FIG. 11 is a flowchart illustrating another example of the remeasurement of the resonant frequency in FIG. 10.

FIG. 11 is a flowchart illustrating another example of the remeasurement of the resonant frequency in FIG. 10.

The position measurement of the capsule endoscope 20, as described above, may be started by obtaining the frequency of the resonant frequency $f_C$ stored in advance. As shown in FIG. 11, alternatively, the position detection device 50 may measure the frequency of the resonant frequency before the position measurement of the capsule endoscope 20 is performed based on the measured resonant frequency. The position measurement is thus not particularly limited.

The frequency of the resonant frequency $f_C$, as described above, may be measured by a sweeping measurement in which the frequency of the alternating magnetic field is changed. Alternatively, the measurement may be simultaneously performed at a plurality of frequencies by applying an alternating magnetic field with a superimposed waveform containing the plurality of frequencies to the LC resonant circuit 43, measuring an induced magnetic field generated by the magnetic induction coil, and subjecting the output to frequency-component separation using, for example, Fourier transformation (BPF).

In this case, the frequencies of the superimposed waveform must have sufficient frequency intervals so as not to affect the component separation.

Second Embodiment

Next, a second embodiment of the present invention will be described with reference to FIGS. 12 and 13.

The basic structure of a position detection system according to this embodiment is the same as that according to the first embodiment, although the structure of the position detection device and the position detection method differ from those according to the first embodiment. In this embodiment, therefore, only the position detection device and the position detection method, and their peripheries, will be described with reference to FIGS. 12 and 13, and a description of the capsule endoscope and so on will be omitted.

Figure 12:
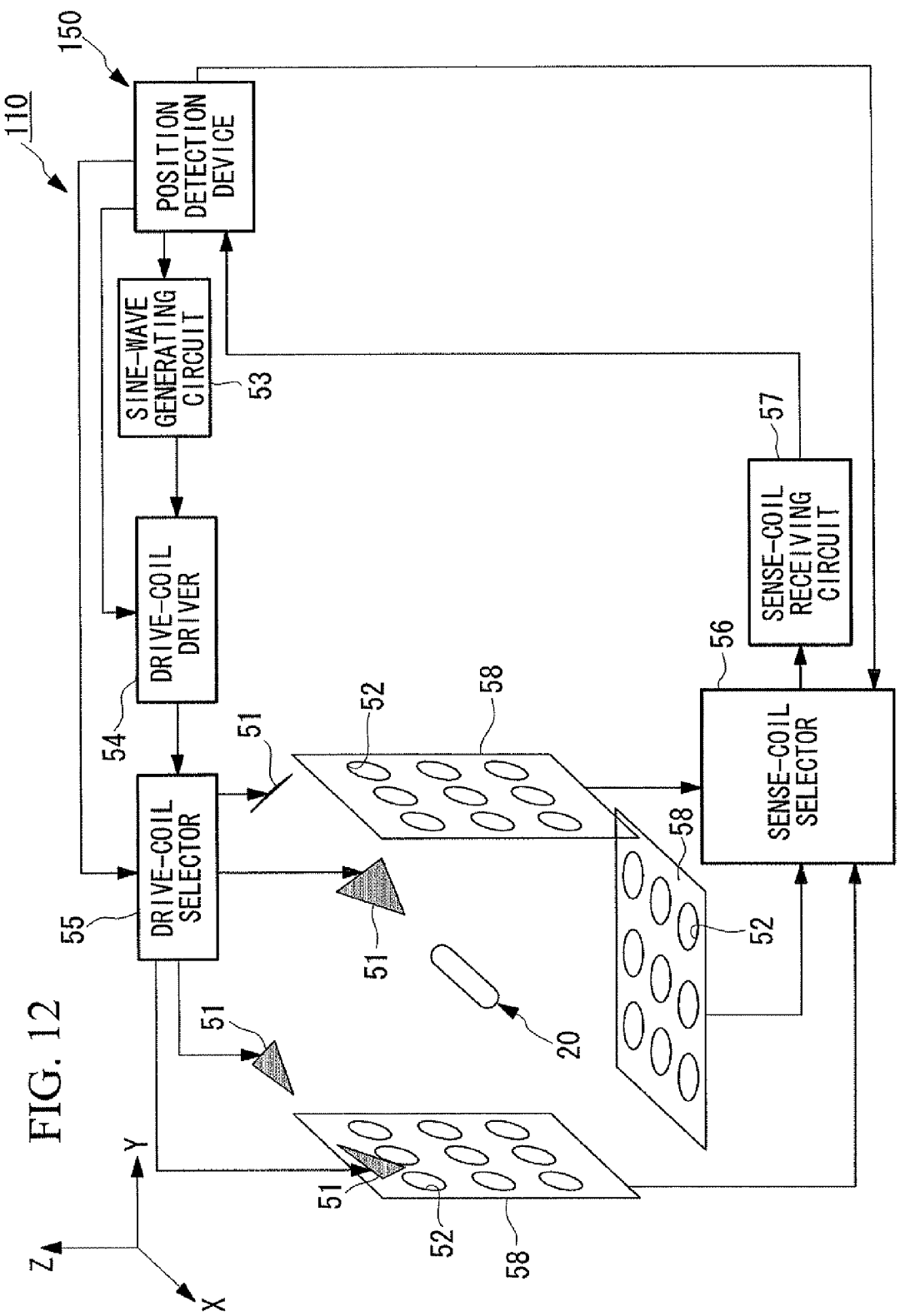
FIG. 12 is a schematic view illustrating the overall structure of a position detection system according to a second embodiment of the present invention.

FIG. 12 is a schematic view illustrating the overall structure of the position detection system according to this embodiment.

The same components as those according to the first embodiment will be denoted by the same reference numerals, and a description thereof will be omitted.

As shown in FIG. 12, a position detection system 110 mainly includes a capsule endoscope 20 that optically images an internal surface of a passage in the body cavity and that wirelessly transmits image signals, and a position detection device (position-analyzing section) 150 that detects the position of the capsule endoscope 20.

As shown in FIG. 12, the position detection device 150 is electrically connected to, for example, drive coils 51 that cause a magnetic induction coil, described below, in the capsule endoscope 20 to generate an induced magnetic field and sense coils 52 that detect the induced magnetic field generated by the magnetic induction coil. The position detection device 150 calculates the position of the capsule endoscope 20 on the basis of the induced magnetic field detected by the sense coils 52 and controls an alternating magnetic field formed by the drive coils 51.

Figure 13:
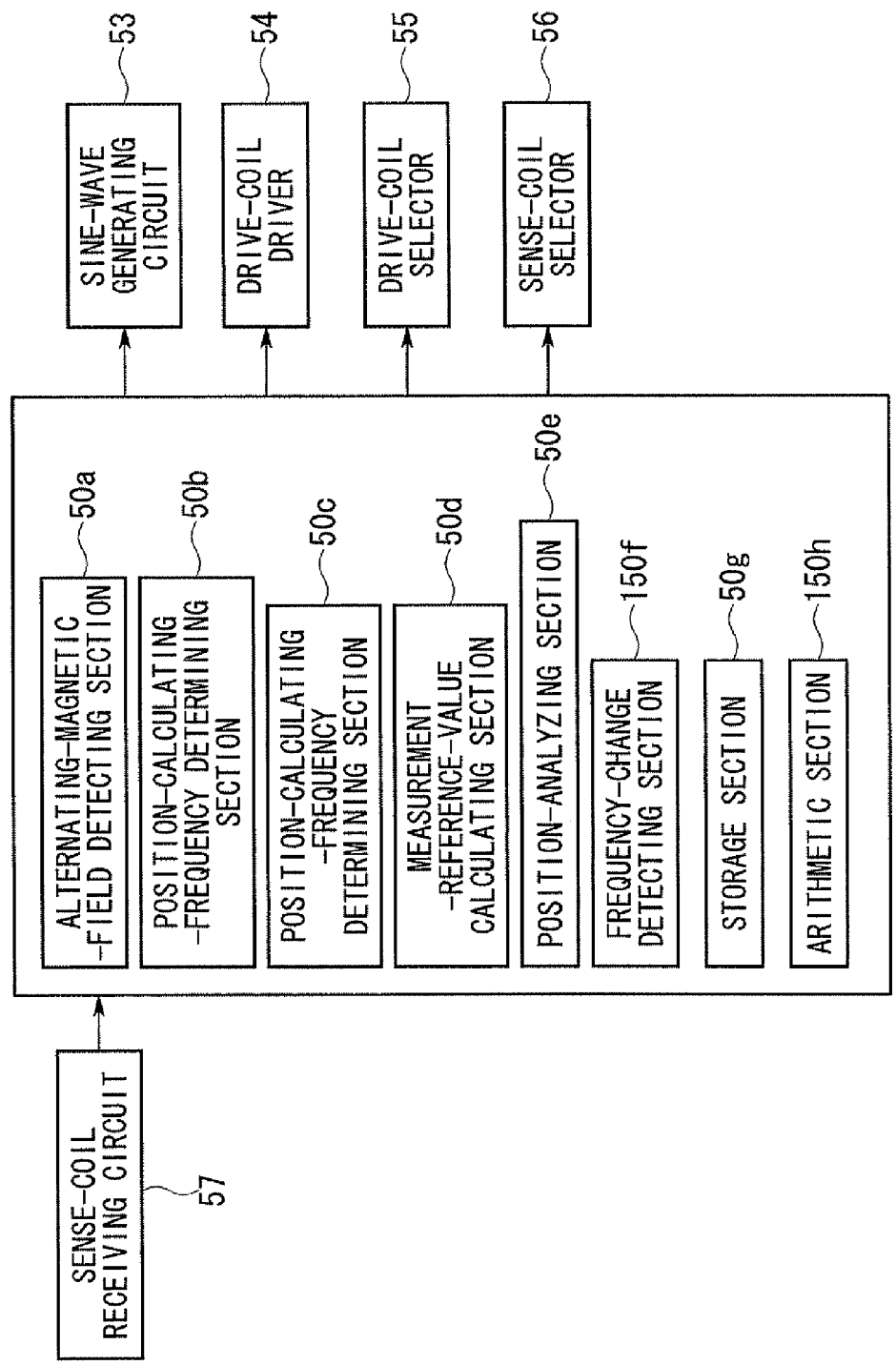
FIG. 13 is a block diagram illustrating the internal structure of a position detection device shown in FIG. 12.

FIG. 13 is a block diagram illustrating the internal structure of the position detection device shown in FIG. 12.

In FIG. 13, the position detection device 150 includes an alternating-magnetic-field detecting section 50a, a position-calculating-frequency determining section 50b, a reference-value-calculating-frequency determining section 50c, a measurement-reference-value calculating section 50d, position-analyzing section 50e, a frequency-change detecting section 150f, a storage section 50g, and an arithmetic section 150h.

The frequency-change detecting section 150f detects a change in the resonant frequency $f_C$ of the LC resonant circuit 43 based on difference measurement values obtained by sweeping over a predetermined frequency range including the position-calculating frequencies $f_H$ and $f_L$. Based on the detected change in the resonant frequency $f_C$, the frequency-change detecting section 150f informs the arithmetic section 150h about the timing of calculating the frequency of the changed resonant frequency $f_C$ and also informs the position-calculating-frequency determining section 50b about the timing of redetermination of the position-calculating frequencies $f_H$ and $f_L$.

The arithmetic section 150h calculates the frequency of the changed resonant frequency $f_C$ of the LC resonant circuit 43 based on the difference measurement values at the position-calculating frequencies $f_H$ and $f_L$.

Next, the operation of the position detection system 110 having the above-described configuration will be described.

The operation of the position detection system 110 is the same as that according to the first embodiment, and a description thereof will therefore be omitted. In addition, the operation of the position detection device 150 and the calculation of the frequencies of the position-calculating frequencies $f_H$ and $f_L$, and the measurement reference values are the same as those according to the first embodiment, and a description thereof will therefore be omitted.

Next, the remeasurement of the resonant frequency of the LC resonant circuit 43, which is a feature of this embodiment, will be described.

When the position measurement of the capsule endoscope 20 is performed, as shown in FIG. 13, the frequency-change detecting section 150f calculates the balance between the difference measurement values at the frequencies of the position-calculating frequencies $f_H$ and $f_L$ calculated by the position-analyzing section 50e. The calculated balance is stored in the storage section 50g. The balance between the difference measurement values may be, for example, the ratio or difference between the two difference measurement values.

If the resonant frequency $f_C$ of the LC resonant circuit 43 is substantially equal to the resonant frequency based on the position-calculating frequencies $f_H$ and $f_L$, the difference measurement values of the position-calculating frequencies $f_H$ and $f_L$ are substantially equal. Normally, the resonant frequency $f_C$ of the LC resonant circuit 43 and the resonant frequency $f_C$ used for position detection are substantially equal immediately after the position detection device 150 starts the position detection.

Thereafter, when the position measurement of the capsule endoscope 20 is performed, the frequency-change detecting section 150f calculates the balance between the difference measurement values at the frequencies of the position-calculating frequencies $f_H$ and $f_L$ and compares it with the balance stored in the storage section 50g. If the difference between the two balances exceeds a predetermined value according to the results of the comparison, the frequency-change detecting section 150f outputs an instruction for frequency redetermination to the arithmetic section 150h and the position-calculating-frequency determining section 50b. If the difference between the two balances does not exceed the predetermined value, the position measurement of the capsule endoscope 20 is continued.

The arithmetic section 150h fed with the instruction from the frequency-change detecting section 150f calculates the frequency of the changed resonant frequency $f_C$ of the LC resonant circuit 43 based on the difference measurement values at the position-calculating frequencies $f_H$ and $f_L$. Based on the results of calculation by the arithmetic section 150h, the position-calculating-frequency determining section 50b redetermines the frequencies of new position-calculating frequencies $f_H$ and $f_L$.

Specifically, the position-calculating-frequency determining section 50b redetermines the frequencies of the new position-calculating frequencies $f_H$ and $f_L$ by changing (sweeping) the frequency of the alternating magnetic field within a predetermined frequency range centered on the changed resonant frequency $f_C$.

After the frequencies of the new position-calculating frequencies $f_H$ and $f_L$ are redetermined, the position detection device 150 calculates the position and so on of the capsule endoscope 20 based on the frequencies of the new position-calculating frequencies $f_H$ and $f_L$.

Subsequently, the above control is repeated until the detection of the position and so on of the capsule endoscope 20 is terminated.

The above configuration includes the frequency-change detecting section 150f to detect a change in the resonant frequency of the LC resonant circuit 43, and the position-calculating-frequency determining section 50b redetermines the position-calculating frequencies $f_H$ and $f_L$ based on the detected change in the resonant frequency. Hence, even if the resonant frequency of the LC resonant circuit 43 is changed with, for example, changes in temperature or environment, the position or orientation of the capsule endoscope 20 can be detected with the optimum position-calculating frequencies $f_H$ and $f_L$ based on the changed resonant frequency.

The timing of redetermination of the position-calculating frequencies $f_H$ and $f_L$ is based on changes in the resonant frequency of the LC resonant circuit 43. This method allows detection of the position or orientation of the capsule endoscope 20 with the optimum position-calculating frequencies $f_H$ and $f_L$ even if the resonant frequency of the LC resonant circuit 43 is suddenly changed, in comparison with, for example, the method of redetermination based on predetermined time intervals.

The frequency-change detecting section 150f can detect a change in the resonant frequency of the LC resonant circuit 43 because it detects the change in the resonant frequency based on difference measurement values obtained by sweeping over a predetermined frequency range including the position-calculating frequencies $f_H$ and $f_L$.

Even if the resonant frequency of the LC resonant circuit 43 is changed, the frequency-change detecting section 150f can detect the changed resonant frequency because the frequency-change detecting section 150f performs the sweeping over the predetermined frequency range, which includes the frequency of the changed resonant frequency.

The frequency-change detecting section 150f can detect a change in the resonant frequency of the LC resonant circuit 43 because it detect the change in the resonant frequency based on the ratio of the difference measurement value at the position-calculating frequency $f_H$ to that at the position-calculating frequency $f_L$.

The difference-measurement-value ratio before the resonant frequency is changed differs from that after the resonant frequency is changed. The frequency-change detecting section 150f can therefore detect a change in the resonant frequency. Specifically, the difference-measurement-value ratio is the ratio of the difference measurement value at the position-calculating frequency $f_H$ in the vicinity of the resonant frequency to that at the position-calculating frequency $f_L$ in the vicinity of the resonant frequency. As the resonant frequency is changed, the difference measurement values at the position-calculating frequencies $f_H$ and $f_L$ are changed, and the difference-measurement-value ratio is changed accordingly. The frequency-change detecting section 150f can detect the change in the resonant frequency by detecting the change in the difference-measurement-value ratio.

The arithmetic section 150h is provided so that it can determine the changed resonant frequency of the LC resonant circuit 43 based on the difference measurement values at the position-calculating frequencies $f_H$ and $f_L$. This allows determination of the position-calculating frequencies $f_H$ and $f_L$ that are two different frequencies in the vicinity of the changed resonant frequency.

The difference measurement values at the position-calculating frequencies $f_H$ and $f_L$ are changed with a change in the resonant frequency. In addition, since the position-calculating frequencies $f_H$ and $f_L$ are different frequencies, the rate of change with the change in the resonant frequency differs between the difference measurement values at the position-calculating frequencies $f_H$ and $f_L$. The arithmetic section 150h can therefore determine the changed resonant frequency based on the changes in the difference measurement values at the position-calculating frequencies $f_H$ and $f_L$ by calculation.

Third Embodiment

Next, a third embodiment of the present invention will be described with reference to FIGS. 14 to 16.

The basic structure of a position detection system according to this embodiment is the same as that according to the first embodiment, although the structure of the position detection device and the position detection method differ from those according to the first embodiment. In this embodiment, therefore, only the position detection device and the position detection method, and their peripheries, will be described with reference to FIGS. 14 to 16, and a description of the capsule endoscope and so on will be omitted.

Figure 14:
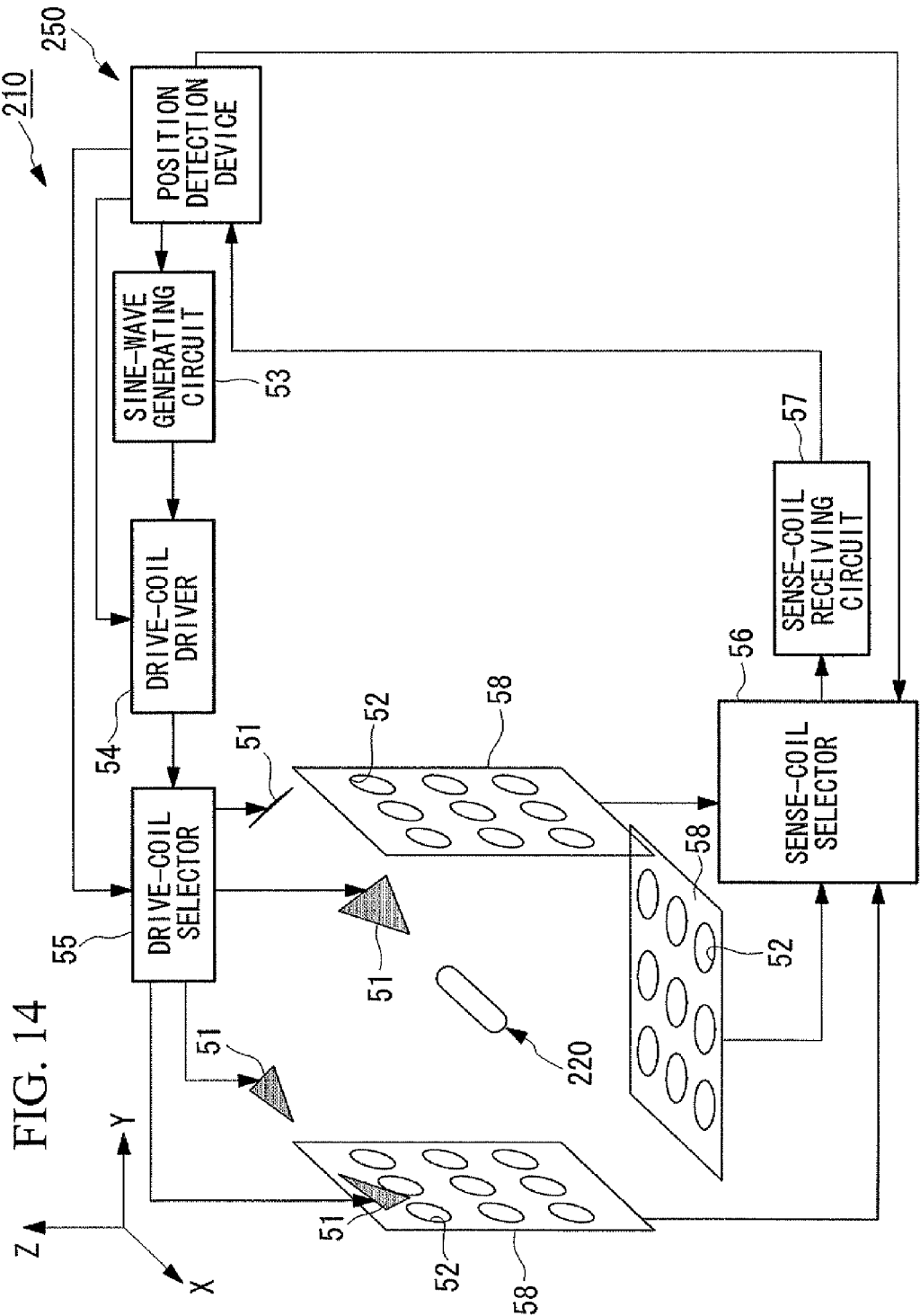
FIG. 14 is a schematic view illustrating the overall structure of a position detection system according to a third embodiment of the present invention.

FIG. 14 is a schematic view illustrating the overall structure of the position detection system according to this embodiment.

The same components as those according to the first embodiment will be denoted by the same reference numerals, and a description thereof will be omitted.

As shown in FIG. 14, a position detection system 210 mainly includes a capsule endoscope 20 that optically images an internal surface of a passage in the body cavity and that wirelessly transmits image signals and a position detection device (position-analyzing section) 250 that detects the position of the capsule endoscope 20.

As shown in FIG. 14, the position detection device 250 is electrically connected to, for example, drive coils 51 that cause a magnetic induction coil, described below, in the capsule endoscope 20 to generate an induced magnetic field and sense coils 52 that detect the induced magnetic field generated by the magnetic induction coil. The position detection device 250 calculates the position of the capsule endoscope 20 on the basis of the induced magnetic field detected by the sense coils 52 and controls an alternating magnetic field formed by the drive coils 51.

Figure 15:
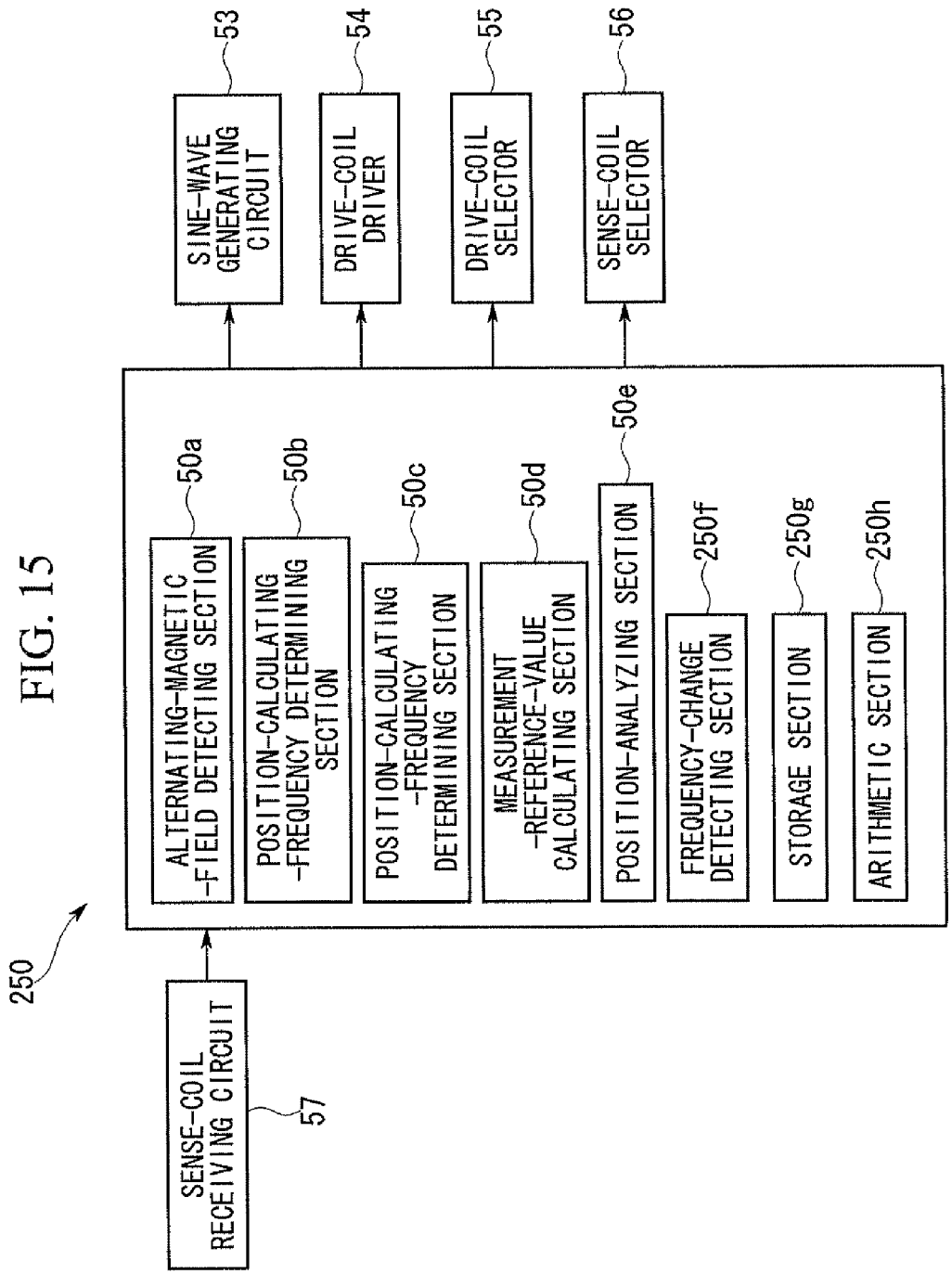
FIG. 15 is a block diagram illustrating the internal structure of a position detection device shown in FIG. 14.

FIG. 15 is a block diagram illustrating the internal structure of the position detection device shown in FIG. 14.

In FIG. 15, the position detection device 250 includes an alternating-magnetic-field detecting section 50a, a position-calculating-frequency determining section 50b, a reference-value-calculating-frequency determining section 50c, a measurement-reference-value calculating section 50d, a position-analyzing section 50e, a frequency-change detecting section 250f, a storage section 250g, and an arithmetic section 250h.

The frequency-change detecting section 250f detects a change in the resonant frequency $f_C$ of the LC resonant circuit 43 based on difference measurement values obtained by sweeping over a predetermined frequency range including the position-calculating frequencies $f_H$ and $f_L$. Based on the detected change in the resonant frequency $f_C$ the frequency-change detecting section 250f informs the arithmetic section 250h about the timing of calculating the frequency of the changed resonant frequency $f_C$ and also informs the position-calculating-frequency determining section 50b about the timing of redetermination of the position-calculating frequencies $f_H$ and $f_L$.

The arithmetic section 250h calculates the frequency of the changed resonant frequency $f_C$ of the LC resonant circuit 43 based on a difference measurement value at the resonant frequency $f_C$ stored in the storage section 250g and the difference measurement values at the position-calculating frequencies $f_H$ and $f_L$.

The storage section 250g stores the resonant frequency $f_C$ of the LC resonant circuit 43 and measurement reference values calculated by the measurement-reference-value calculating section 50d.

Next, the operation of the position detection system 210 having the above-described configuration will be described.

The operation of the position detection system 210 is the same as that according to the first embodiment, and a description thereof will therefore be omitted. In addition, the operation of the position detection device 250 and the calculation of the frequencies of the position-calculating frequencies $f_H$ and $f_L$ and the measurement reference values are the same as those according to the first embodiment, and a description thereof will therefore be omitted.

Next, the remeasurement of the resonant frequency of the LC resonant circuit 43, which is a feature of this embodiment, will be described.

As shown in FIG. 15, first, the position detection device 250 stores the frequency of the resonant frequency $f_C$ of the LC resonant circuit 43 in the storage section 250g. Normally, the resonant frequency $f_C$ of the LC resonant circuit 43 and the resonant frequency $f_C$ used for position detection are substantially equal immediately after the position detection device 250 starts the position detection. Hence, the difference measurement value at the resonant frequency $f_C$ stored in the storage section 250g is zero.

Thereafter, when the position measurement of the capsule endoscope 20 is performed, the frequency-change detecting section 250f calculates the difference measurement value at the resonant frequency $f_C$ stored in the storage section 250g. If the calculated difference measurement value is a value other than zero, the frequency-change detecting section 250f outputs an instruction for frequency redetermination to the arithmetic section 250h and the position-calculating-frequency determining section 50b. If the calculated difference measurement value is zero, the position measurement of the capsule endoscope 20 is continued.

The arithmetic section 250h fed with the instruction from the frequency-change detecting section 250f calculates the frequency of the changed resonant frequency $f_C$ of the LC resonant circuit 43 based on the difference measurement value at the stored resonant frequency $f_C$ and one of the difference measurement values at the position-calculating frequencies $f_H$ and $f_L$, whichever one has a different sign from the difference measurement value at the stored resonant frequency $f_C$. Based on the results of calculation by the arithmetic section 250h, the position-calculating-frequency determining section 50b redetermines the frequencies of new position-calculating frequencies $f_H$ and $f_L$.

Specifically, the position-calculating-frequency determining section 50b redetermines the frequencies of the new position-calculating frequencies $f_H$ and $f_L$ by changing (sweeping) the frequency of the alternating magnetic field within a predetermined frequency range centered on the changed resonant frequency $f_C$.

Figure 16:
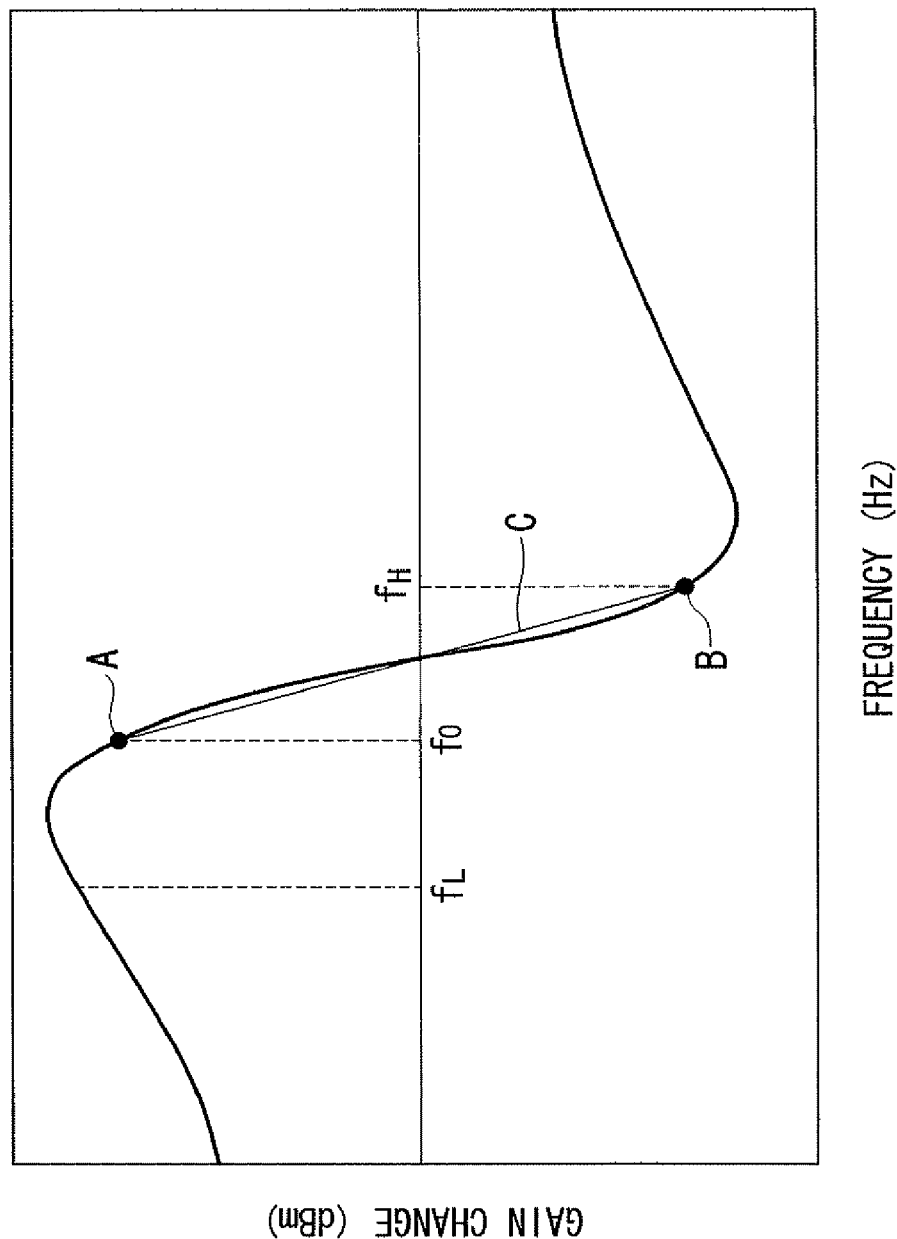
FIG. 16 is a graph illustrating a method for calculating a changed resonant frequency in an arithmetic section shown in FIG. 15.

FIG. 16 is a graph illustrating a method for calculating the changed resonant frequency $f_C$ in the arithmetic section shown in FIG. 15.

The method for calculating the changed resonant frequency $f_C$ in the arithmetic section 250h will now be described.

In FIG. 16, the arithmetic section 250h calculates a line segment (C) between the difference measurement value (A) at the stored resonant frequency $f_C$ and, of the difference measurement values at the position-calculating frequencies $f_H$ and $f_L$, the difference measurement value (B) having a different sign from the difference measurement value at the stored resonant frequency. If the resonant frequency $f_C$ of the LC resonant circuit 43 is significantly changed, the line segment (C) approximates to a curve representing the frequency characteristics of the LC resonant circuit 43 in the vicinity of the resonant frequency $f_C$ of the LC resonant circuit 43. As the changed resonant frequency $f_C$, the arithmetic section 250h determines the frequency at which the gain change is zero on the line segment (C).

According to the above configuration, including the storage section 250g, the frequency-change detecting section 250f can detect a change in the resonant frequency $f_C$ of the LC resonant circuit 43 based on the difference measurement value at the resonant frequency $f_C$ retrieved from the storage section 250g.

If, for example, the resonant frequency $f_C$ of the LC resonant circuit 43 is equal to the resonant frequency $f_C$ stored in the storage section 250g, the difference measurement value calculated at the resonant frequency $f_C$ is zero. If the resonant frequency $f_C$ of the LC resonant circuit 43 is changed and therefore no longer agrees with the resonant frequency $f_C$ stored in the storage section 250g, the difference measurement value calculated at the resonant frequency $f_C$ stored in the storage section 250g is a value other than zero.

Thus, the frequency-change detecting section 250f can detect the change in the resonant frequency $f_C$ of the LC resonant circuit 43 based on the difference measurement value calculated at the resonant frequency $f_C$ stored in the storage section 250g.

The difference measurement value calculated at the stored resonant frequency $f_C$ is zero if the frequency is equal to the resonant frequency $f_C$ of the LC resonant circuit 43 and is a value other than zero in other cases. This method can determine whether or not the resonant frequency $f_C$ stored in the storage section 250g is equal to the resonant frequency $f_C$ of the LC resonant circuit 43 more accurately than, for example, the method using the difference-measurement-value ratio of the position-calculating frequencies $f_H$ and $f_L$ in the vicinity of the resonant frequency $f_C$. This contributes to increased responsiveness to changes in the resonant frequency $f_C$ of the LC resonant circuit 43.

The arithmetic section 250h calculates the resonant frequency $f_C$ of the LC resonant circuit 43 based on the difference measurement value at the resonant frequency $f_C$ stored in the storage section 250g and, of the difference measurement values at the position-calculating frequencies $f_H$ and $f_L$, a difference measurement value having a different sign from the difference measurement value at the stored resonant frequency $f_C$. Hence, even if the resonant frequency $f_C$ of the LC resonant circuit 43 is significantly changed, the arithmetic section 250h can accurately redetermine the changed resonant frequency $f_C$. As a result, the position-calculating-frequency determining section 50b can redetermine the frequencies of the position-calculating frequencies $f_H$ and $f_L$ based on the redetermined resonant frequency $f_C$.

As shown in FIG. 16, the line segment (C) can be formed between the difference measurement value (A) at the stored resonant frequency $f_C$ and, of the difference measurement values at the position-calculating frequencies $f_H$ and $f_L$, the difference measurement value (B) having a different sign from the difference measurement value at the stored resonant frequency $f_C$. If the resonant frequency $f_C$ of the LC resonant circuit 43 is significantly changed, the line segment (C) approximates to a curve representing the frequency characteristics of the LC resonant circuit 43 in the vicinity of the resonant frequency $f_C$ of the LC resonant circuit 43. With the line segment (C), therefore, the arithmetic section 250h can more accurately redetermine the resonant frequency $f_C$ of the LC resonant circuit 43 after a significant change in the resonant frequency $f_C$.

Fourth Embodiment

Next, a fourth embodiment of the present invention will be described with reference to FIGS. 17 and 18.

The basic structure of a position detection system according to this embodiment is the same as that according to the first embodiment, although the structure of the position detection device and the position detection method differ from those according to the first embodiment. In this embodiment, therefore, only the position detection device and the position detection method, and their peripheries, will be described with reference to FIGS. 17 and 18, and a description of the capsule endoscope and so on will be omitted.

Figure 17:
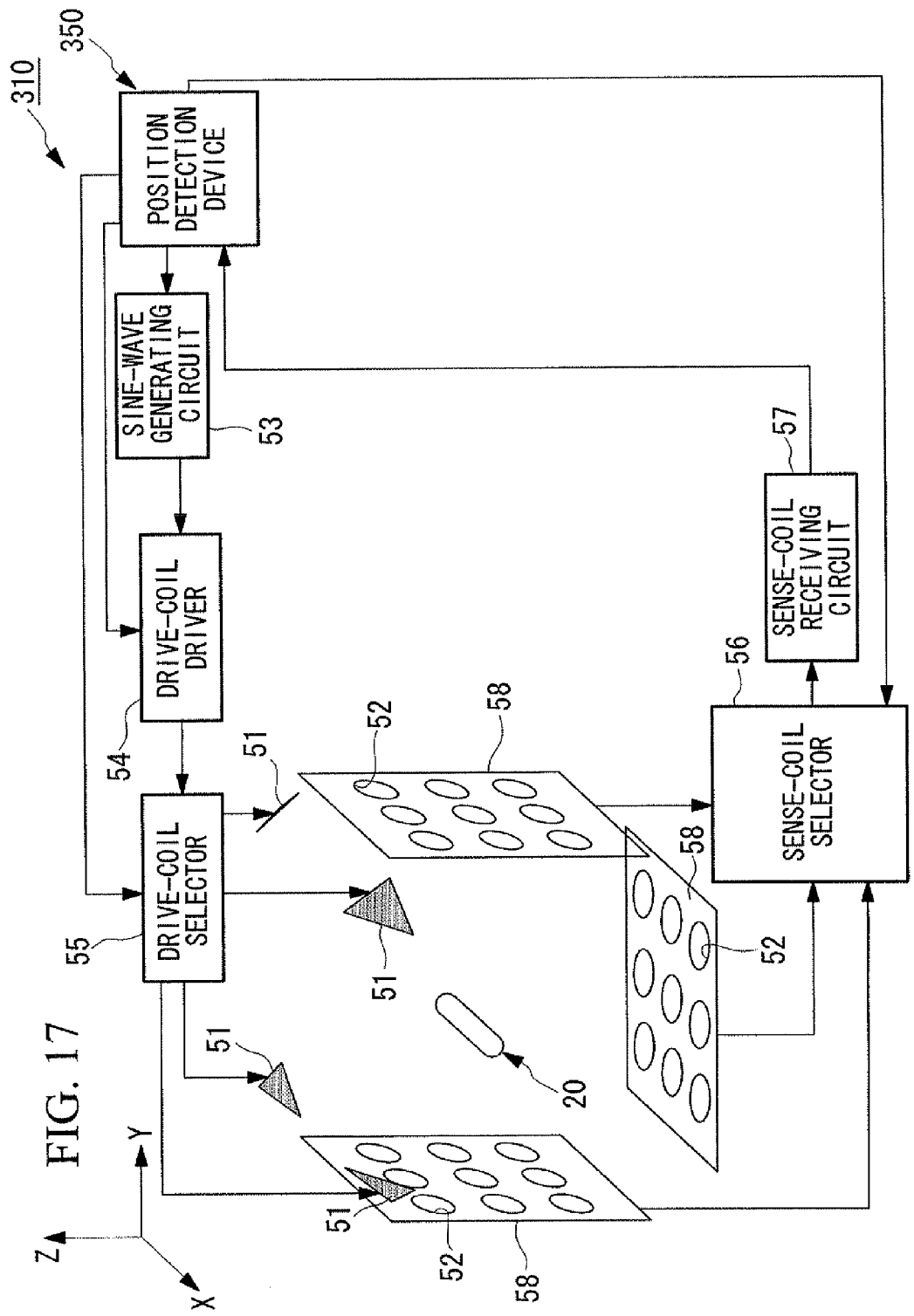
FIG. 17 is a schematic view illustrating the overall structure of a position detection system according to a fourth embodiment of the present invention.

FIG. 17 is a schematic view illustrating the overall structure of the position detection system according to this embodiment.

The same components as those according to the first embodiment will be denoted by the same reference numerals, and a description thereof will be omitted.

As shown in FIG. 17, a position detection system 310 mainly includes a capsule endoscope 20 that optically images an internal surface of a passage in the body cavity and that wirelessly transmits image signals and a position detection device (position-analyzing section) 350 that detects the position of the capsule endoscope 20.

As shown in FIG. 17, the position detection device 350 is electrically connected to, for example, drive coils 51 that cause a magnetic induction coil, described below, in the capsule endoscope 20 to generate an induced magnetic field and sense coils 52 that detect the induced magnetic field generated by the magnetic induction coil. The position detection device 350 calculates the position of the capsule endoscope 20 on the basis of the induced magnetic field detected by the sense coils 52 and controls an alternating magnetic field formed by the drive coils 51.

FIG. 18 is a block diagram illustrating the internal structure of the position detection device shown in FIG. 17.

In FIG. 18, the position detection device 350 includes an alternating-magnetic-field detecting section 50a, a position-calculating-frequency determining section 50b, a reference-value-calculating-frequency determining section 50c, a measurement-reference-value calculating section 50d, a position-analyzing section 350e, a frequency-change detecting section 350f, and a storage section 350g.

The position-analyzing section 350e calculates a first magnetic-field strength of an alternating magnetic field from the magnetic induction coil 42 based on the output of the magnetic sensors 52 and measurement reference values and also calculates the positional relationship between the capsule endoscope 20 and the drive coils 51. The frequency-change detecting section 350f detects a change in resonant frequency based on the difference between the first magnetic-field strength and a second magnetic-field strength of the alternating magnetic field from the magnetic induction coil, which is determined from the positional relationship between the capsule endoscope 20 and the drive coils 51. The storage section 350g stores a comparison between the first and second magnetic-field strengths.

Of the strengths of the magnetic field generated by the magnetic induction coil 42, the first magnetic-field strength is a magnetic-field strength carrying information about the actual positional relationship between the drive coils 51 and the magnetic induction coil 42. The second magnetic-field strength is a magnetic-field strength calculated from the positional relationship between the position of the drive coils 51 and the calculated position of the magnetic induction coil 42 and the value of the resonant frequency $f_C$.

Next, the operation of the position detection system 310 having the above-described configuration will be described.

The operation of the position detection system 310 is the same as that according to the first embodiment, and a description thereof will therefore be omitted. In addition, the operation of the position detection device 350 and the calculation of the frequencies of the position-calculating frequencies $f_H$ and $f_L$ the measurement reference values are the same as those according to the first embodiment, and a description thereof will therefore be omitted.

Next, the remeasurement of the resonant frequency of the LC resonant circuit 43, which is a feature of this embodiment, will be described.

As shown in FIG. 18, first, the position-analyzing section 350e calculates the first magnetic-field strength of the alternating magnetic field from the magnetic induction coil 42 based on the output of the magnetic sensors 52 and the measurement reference values. The position-analyzing section 350e also calculates the positional relationship between the capsule endoscope 20 and the drive coils 51. The frequency-change detecting section 350f calculates the second magnetic-field strength of the alternating magnetic field from the magnetic induction coil from the calculated positional relationship between the capsule endoscope 20 and the drive coils 51 and then calculates the difference between the calculated first magnetic-field strength and the calculated second magnetic-field strength. The calculated difference is stored in the storage section 350g.

Thereafter, when the position measurement of the capsule endoscope 20 is performed, the frequency-change detecting section 250f calculates the first magnetic-field strength again, and the position-analyzing section 350e calculates the second magnetic-field strength and then calculates the difference between the first magnetic-field strength and the second magnetic-field strength. Once the new difference is calculated, the position detection device 350 compares the new difference with the difference stored in the storage section 350g. If the difference between the stored difference and the new difference exceeds a predetermined value, the position detection device 350 outputs an instruction for frequency redetermination to the position-calculating-frequency determining section 50b. If the difference between the stored difference and the new difference does not exceed the predetermined value, the position measurement of the capsule endoscope 20 is continued.

When the frequencies of the new position-calculating frequencies $f_H$ and $f_L$ are redetermined, the position detection device 350 calculates the position and so on of the capsule endoscope 20 based on the frequencies of the new position-calculating frequencies $f_H$ and $f_L$.

Subsequently, the above control is repeated until the detection of the position and so on of the capsule endoscope 20 is terminated.

According to the above configuration, the position-analyzing section 350e calculates the first magnetic-field strength when calculating the position of the magnetic induction coil 42. The frequency-change detecting section 350f then calculates the second magnetic-field strength from the relationship between the calculated position and orientation of the magnetic induction coil 42 and the position and orientation of the drive coils 51. If the resonant frequency $f_C$ of the magnetic induction coil 42 is changed, the first and second magnetic-field strengths have different values. The frequency-change detecting section 350f can then detect the change in the resonant frequency $f_C$ of the magnetic induction coil 42 by comparing the first and second magnetic-field strengths.

Of the strengths of the magnetic field generated by the magnetic induction coil 42, the first magnetic-field strength is a magnetic-field strength carrying information about the actual positional relationship between the drive coils 51 and the magnetic induction coil 42. The second magnetic-field strength is a magnetic-field strength calculated from the positional relationship between the position of the drive coils 51 and the calculated position of the magnetic induction coil 42 and the value of the resonant frequency $f_C$.

All embodiments described above are embodiments applied to a capsule endoscope or a capsule medical device.

The present invention, however, is not limited to the above embodiments; it may be applied to any medical device for use in a body cavity, such as an endoscope device, a catheter device, or forceps. Furthermore, the invention encompasses various combinations of the embodiments.

The invention claimed is:

1. A position detection system comprising:
    a device having a magnetic induction coil;
    a driving coil that generates an alternating magnetic field to be applied to the magnetic induction coil, the alternating magnetic field having a position-calculating frequency in the vicinity of a resonant frequency of the magnetic induction coil;
    a plurality of magnetic sensors that detects an induced magnetic field generated by the magnetic induction coil when the alternating magnetic field is applied thereto;
    a measurement-reference-value calculating section that determines a measurement reference value at the position-calculating frequency, based on an output of the magnetic sensors at the position-calculating frequency when only the alternating magnetic field is applied thereto;
    a position-analyzing section that calculates at least one of the position and orientation of the device, based on a component at the position-calculating frequency of a difference measurement value that is a difference between an output of the magnetic sensors when the alternating magnetic field and the induced magnetic field are applied thereto and the measurement reference value;
    a frequency-change detecting section that detects a change in frequency characteristics related to the magnetic induction coil from magnetic-field information obtained by the plurality of magnetic sensors; and
    a redetermining section that redetermines the position-calculating frequency at a predetermined timing based on the change in the frequency characteristics.

2. The position detection system according to claim 1, wherein the redetermining section redetermines the position-calculating frequency at predetermined time intervals.

3. The position detection system according to claim 1, wherein the frequency-change detecting section detects the change in the frequency characteristics based on the magnetic-field information, the magnetic-field information being obtained by sweeping over a predetermined frequency range including the position-calculating frequency.

4. The position detection system according to claim 1, wherein
    the position-calculating frequency comprises two different frequencies in the vicinity of the resonant frequency; and
    the frequency-change detecting section calculates the ratio of the difference measurement values at the two different frequencies and detects the change in the frequency characteristics based on the calculated ratio of the difference measurement values.

5. The position detection system according to claim 4, further comprising an arithmetic section that calculates the resonant frequency based on the difference measurement values at the two different frequencies.

6. The position detection system according to claim 1, further comprising a storage section that stores the resonant frequency;
    wherein the frequency-change detecting section detects the change in the frequency characteristics based on the difference measurement value calculated at the resonant frequency retrieved from the storage section.

7. The position detection system according to claim 6, further comprising an arithmetic section that calculates the resonant frequency to be stored in the storage section;
    wherein the arithmetic section calculates the resonant frequency based on the difference measurement value at the resonant frequency retrieved from the storage section and the difference measurement values at a plurality of the position-calculating frequencies.

8. The position detection system according to claim 7, wherein the arithmetic section calculates the resonant frequency based on the difference measurement value at the resonant frequency stored in the storage section and, of the difference measurement values at the plurality of position-calculating frequencies, a difference measurement value having a different sign from the difference measurement value at the stored resonant frequency.

9. The position detection system according to claim 1, wherein
    the position-analyzing section calculates a first magnetic-field strength of the alternating magnetic field from the magnetic induction coil based on the output of the magnetic sensors and the measurement reference value and also calculates the positional relationship between the device and the driving coil; and
    the frequency-change detecting section detects the change in the frequency characteristics based on a difference between the first magnetic-field strength and a second magnetic-field strength of the alternating magnetic field from the magnetic induction coil, the second magnetic-field strength being determined from the positional relationship between the device and the driving coil.

10. The position detection system according to claim 1, wherein the device is a capsule medical device.

11. A position detection method for detecting at least one of the position and orientation of a device having a magnetic induction coil based on an induced magnetic field generated by the magnetic induction coil when an alternating magnetic field having a position-calculating frequency is applied thereto, the method comprising the steps of:
    calculating at least one of the position and orientation of the device based on the induced magnetic field;
    detecting a change in the resonant frequency of the magnetic induction coil from magnetic-field information obtained by the plurality of magnetic sensors;
    redetermining the position-calculating frequency from the change in the resonant frequency; and
    applying an alternating magnetic field having the redetermined position-calculating frequency to the magnetic induction coil to generate an induced magnetic field based on the change in the resonant frequency.

12. The position detection method according to claim 11, wherein the step of calculating at least one of the position and orientation of the device based on the induced magnetic field comprises the steps of:
    determining as a measurement reference value a magnetic-field strength detected at the position-calculating frequency when only the alternating magnetic field acts; and
    calculating at least one of the position and orientation of the device based on a difference between a magnetic-field strength of a combined magnetic field of the alternating magnetic field and the induced magnetic field and the measurement reference value.

* * * * *